(12) United States Patent
Hawley

US011697803B2

(10) Patent No.: US 11,697,803 B2
(45) Date of Patent: Jul. 11, 2023

(54) METHOD OF PROTEIN PURIFICATION FROM E.COLI

(71) Applicant: Ansun Biopharma, Inc., San Diego, CA (US)

(72) Inventor: Stephen Hawley, San Diego, CA (US)

(73) Assignee: Ansun Biopharma, Inc., San Diego, CA (US)

( * ) Notice: Subject to any disclaimer, the term of this patent is extended or adjusted under 35 U.S.C. 154(b) by 0 days.

(21) Appl. No.: 16/511,906

(22) Filed: Jul. 15, 2019

(65) Prior Publication Data

US 2020/0149015 A1 May 14, 2020

Related U.S. Application Data

(63) Continuation of application No. 14/210,728, filed on Mar. 14, 2014, now Pat. No. 10,351,828.

(60) Provisional application No. 61/800,345, filed on Mar. 15, 2013.

(51) Int. Cl.
*C12N 9/00* (2006.01)
*C07K 1/14* (2006.01)
*C12P 21/00* (2006.01)
*C12N 1/06* (2006.01)
*C12N 9/24* (2006.01)

(52) U.S. Cl.
CPC ............... *C12N 9/00* (2013.01); *C07K 1/14* (2013.01); *C12N 1/06* (2013.01); *C12N 9/2402* (2013.01); *C12P 21/00* (2013.01)

(58) Field of Classification Search
None
See application file for complete search history.

(56) References Cited

U.S. PATENT DOCUMENTS

| 7,807,174 | B2 | 10/2010 | Fang et al. |
| 10,351,828 | B2 | 7/2019 | Hawley |
| 2002/0068280 | A1 | 6/2002 | Fairman |
| 2007/0105154 | A1 | 5/2007 | Engel et al. |

FOREIGN PATENT DOCUMENTS

| CN | 1358196 | 7/2002 | |
| JP | 2016502436 | 1/2016 | |
| JP | 6416867 | 10/2018 | |
| WO | WO 9013032 | 11/1990 | |
| WO | WO-02074940 A1 * | 9/2002 | ........... A61K 35/765 |
| WO | WO 2014/152524 | 9/2014 | |

OTHER PUBLICATIONS

Amersham, Inc. Protein_Purification. Published 1999.*
Huang, Separating and purifying glutamic acid decarboxylase from microorganisms by using chromatographic technique comprises e.g. centrifuging microbial cells having expression of glutamic acid decarboxylase to prepare wet cells. English Abstract from CN 107723283, 2018.*
International Preliminary Report on Patentability and Written Opinion in corresponding PCT Application No. PCT/US2014/27436 dated Sep. 24, 2015, 10 pages.
Malakhov, M. et al., "Sialidase Fusion Protein as a Novel Broad-Spectrum Inhibitor of Influenza Virus Infection," Antimicrobial Agents and Chemotherapy. (2006) 50(4):1470-1479.
Danilevich V N et al: "Rapid and efficient extraction of soluble proteins from Gram-negative microorganisms without disruption of cell walls," Russian Journal of Bioorganic Chemistry, Dec. 1, 2006, 32(6):521-528.
Extended European Search Report in European Application No. 14770943.0, dated Oct. 6, 2016, 6 pages.
International Search Report and Written Opinion in corresponding PCT Application No. PCT/US2014/27436 dated Sep. 19, 2014, pp. 1-12.
Danilevich et al., "Rapid and efficient extraction of soluble proteins from gram-negative microorganisms without disruption of cell walls," Russian Journal of Bioorganic Chemistry, Dec. 2006, 32(6):521-528.
Michael et al., "Sialidase Fusion Protein as a Novel Broad-Spectrum Inhibitor of Influenza Virus Infection," Antimicrobial Agents and Chemotherapy, Apr. 2006, 50(4):1470-1479.
Office Action in Chinese Appln. No. 2019102627284, dated Sep. 8, 2022, 13 pages (with English translation).

* cited by examiner

*Primary Examiner* — Tekchand Saidha
(74) *Attorney, Agent, or Firm* — Fish & Richardson P.C.

(57) ABSTRACT

The present disclosure provides methods for releasing intracellular proteins. The method allows isolation of the protein of interest from the cell without the requirement for mechanical disruption of the cells, without the need for isolation of the cells from the culture media, and without the need for removal of the cells from the culture media.

18 Claims, 12 Drawing Sheets

Specification includes a Sequence Listing.

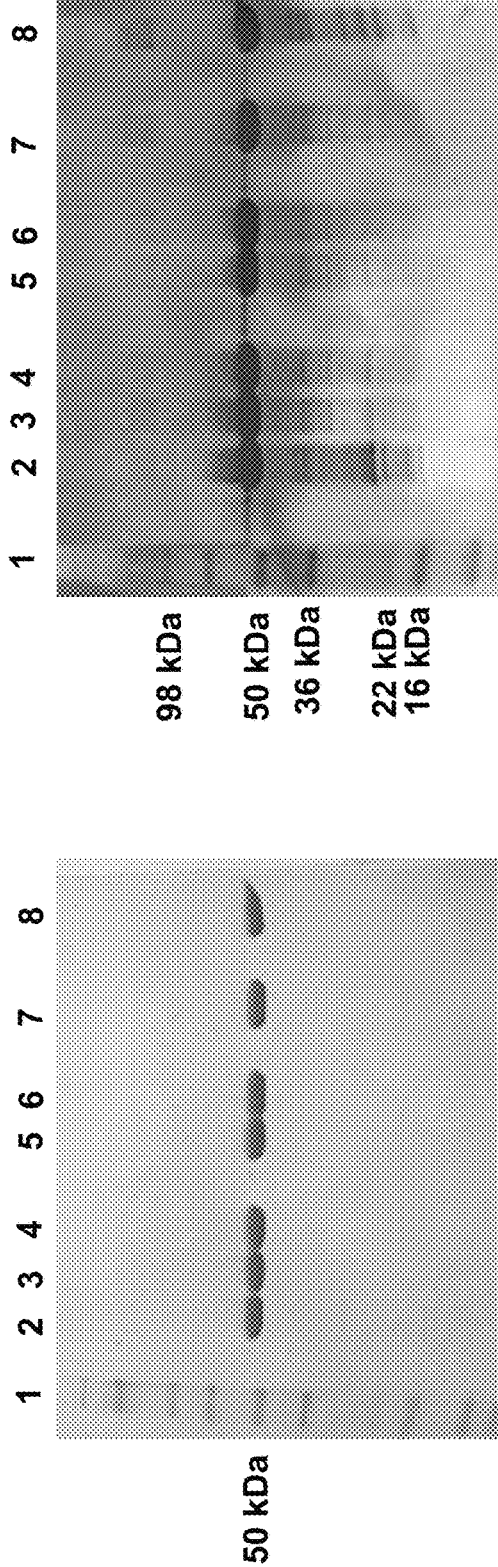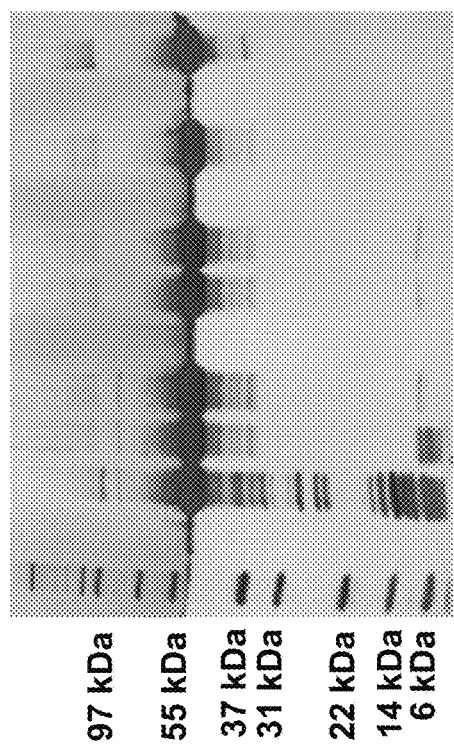

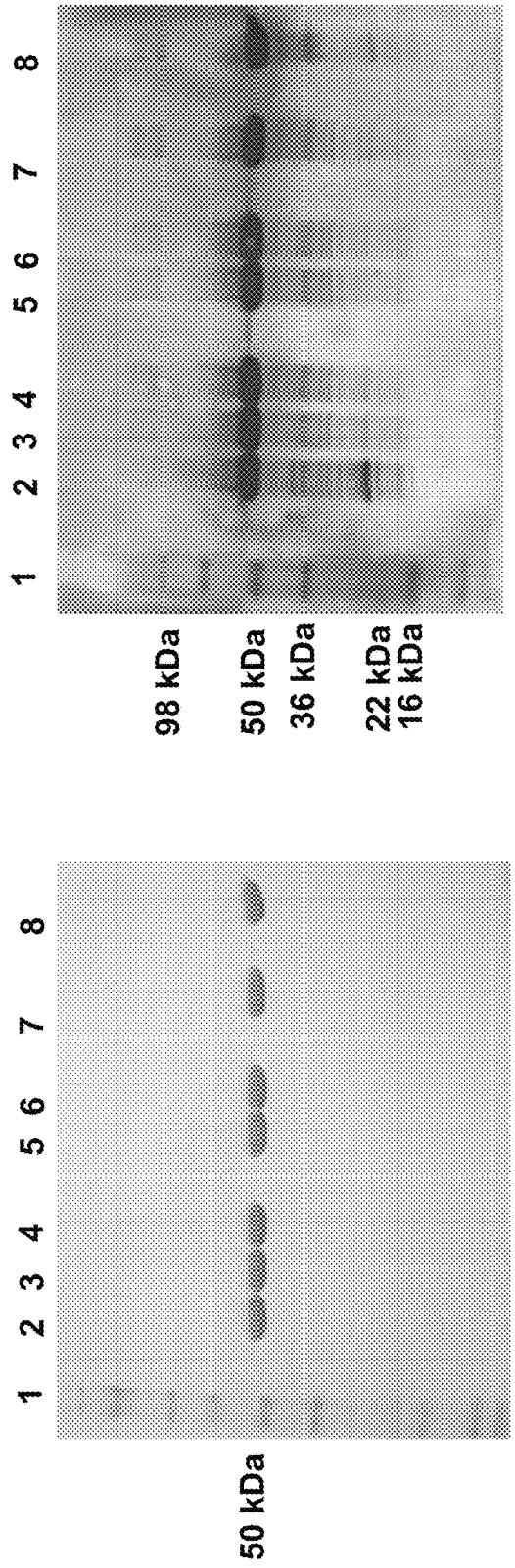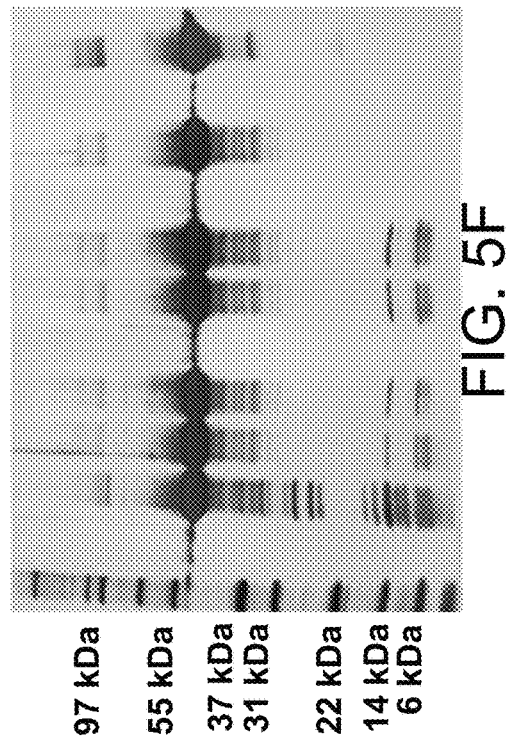

SEQUENCE LISTING

<160> NUMBER OF SEQ ID NOS: 2

<210> SEQ ID NO 1
<211> LENGTH: 414
<212> TYPE: PRT
<213> ORGANISM: Artificial Sequence
<220> FEATURE:
<223> OTHER INFORMATION: synthetic polypeptide

<400> SEQUENCE: 1

Gly Asp His Pro Gln Ala Thr Pro Ala Pro Ala Pro Asp Ala Ser Thr
1               5                   10                  15

Glu Leu Pro Ala Ser Met Ser Gln Ala Gln His Leu Ala Ala Asn Thr
            20                  25                  30

Ala Thr Asp Asn Tyr Arg Ile Pro Ala Ile Thr Thr Ala Pro Asn Gly
        35                  40                  45

Asp Leu Leu Ile Ser Tyr Asp Glu Arg Pro Lys Asp Asn Gly Asn Gly
    50                  55                  60

Gly Ser Asp Ala Pro Asn Pro Asn His Ile Val Gln Arg Arg Ser Thr
65                  70                  75                  80

Asp Gly Gly Lys Thr Trp Ser Ala Pro Thr Tyr Ile His Gln Gly Thr
                85                  90                  95

Glu Thr Gly Lys Lys Val Gly Tyr Ser Asp Pro Ser Tyr Val Val Asp
            100                 105                 110

His Gln Thr Gly Thr Ile Phe Asn Phe His Val Lys Ser Tyr Asp Gln
        115                 120                 125

Gly Trp Gly Gly Ser Arg Gly Gly Thr Asp Pro Glu Asn Arg Gly Ile
    130                 135                 140

Ile Gln Ala Glu Val Ser Thr Ser Thr Asp Asn Gly Trp Thr Trp Thr
145                 150                 155                 160

His Arg Thr Ile Thr Ala Asp Ile Thr Lys Asp Lys Pro Trp Thr Ala
                165                 170                 175

Arg Phe Ala Ala Ser Gly Gln Gly Ile Gln Ile Gln His Gly Pro His
            180                 185                 190

Ala Gly Arg Leu Val Gln Gln Tyr Thr Ile Arg Thr Ala Gly Gly Ala
        195                 200                 205

Val Gln Ala Val Ser Val Tyr Ser Asp Asp His Gly Lys Thr Trp Gln
    210                 215                 220

Ala Gly Thr Pro Ile Gly Thr Gly Met Asp Glu Asn Lys Val Val Glu
225                 230                 235                 240

Leu Ser Asp Gly Ser Leu Met Leu Asn Ser Arg Ala Ser Asp Gly Ser
                245                 250                 255

Gly Phe Arg Lys Val Ala His Ser Thr Asp Gly Gly Gln Thr Trp Ser
            260                 265                 270

Glu Pro Val Ser Asp Lys Asn Leu Pro Asp Ser Val Asp Asn Ala Gln
        275                 280                 285

Ile Ile Arg Ala Phe Pro Asn Ala Ala Pro Asp Asp Pro Arg Ala Lys
    290                 295                 300

Val Leu Leu Leu Ser His Ser Pro Asn Pro Arg Pro Trp Ser Arg Asp
305                 310                 315                 320

Arg Gly Thr Ile Ser Met Ser Cys Asp Asp Gly Ala Ser Trp Thr Thr
                325                 330                 335

Ser Lys Val Phe His Glu Pro Phe Val Gly Tyr Thr Thr Ile Ala Val
            340                 345                 350

```
Gln Ser Asp Gly Ser Ile Gly Leu Leu Ser Glu Asp Ala His Asn Gly
            355                 360                 365

Ala Asp Tyr Gly Gly Ile Trp Tyr Arg Asn Phe Thr Met Asn Trp Leu
370                 375                 380

Gly Glu Gln Cys Gly Gln Lys Pro Ala Lys Lys Lys Gly Gly
385                 390                 395                 400

Lys Asn Gly Lys Asn Arg Arg Asn Arg Lys Lys Lys Asn Pro
                405                 410
```

<210> SEQ ID NO 2
<211> LENGTH: 415
<212> TYPE: PRT
<213> ORGANISM: Artificial Sequence
<220> FEATURE:
<223> OTHER INFORMATION: synthetic polypeptide

<400> SEQUENCE: 2

```
Met Gly Asp His Pro Gln Ala Thr Pro Ala Pro Ala Pro Asp Ala Ser
1               5                   10                  15

Thr Glu Leu Pro Ala Ser Met Ser Gln Ala Gln His Leu Ala Ala Asn
                20                  25                  30

Thr Ala Thr Asp Asn Tyr Arg Ile Pro Ala Ile Thr Thr Ala Pro Asn
            35                  40                  45

Gly Asp Leu Leu Ile Ser Tyr Asp Glu Arg Pro Lys Asp Asn Gly Asn
50                  55                  60

Gly Gly Ser Asp Ala Pro Asn Pro Asn His Ile Val Gln Arg Arg Ser
65                  70                  75                  80

Thr Asp Gly Gly Lys Thr Trp Ser Ala Pro Thr Tyr Ile His Gln Gly
                85                  90                  95

Thr Glu Thr Gly Lys Lys Val Gly Tyr Ser Asp Pro Ser Tyr Val Val
            100                 105                 110

Asp His Gln Thr Gly Thr Ile Phe Asn Phe His Val Lys Ser Tyr Asp
            115                 120                 125

Gln Gly Trp Gly Gly Ser Arg Gly Gly Thr Asp Pro Glu Asn Arg Gly
    130                 135                 140

Ile Ile Gln Ala Glu Val Ser Thr Ser Thr Asp Asn Gly Trp Thr Trp
145                 150                 155                 160

Thr His Arg Thr Ile Thr Ala Asp Ile Thr Lys Asp Lys Pro Trp Thr
                165                 170                 175

Ala Arg Phe Ala Ala Ser Gly Gln Gly Ile Gln Ile Gln His Gly Pro
            180                 185                 190

His Ala Gly Arg Leu Val Gln Gln Tyr Thr Ile Arg Thr Ala Gly Gly
            195                 200                 205

Ala Val Gln Ala Val Ser Val Tyr Ser Asp Asp His Gly Lys Thr Trp
    210                 215                 220

Gln Ala Gly Thr Pro Ile Gly Thr Gly Met Asp Glu Asn Lys Val Val
225                 230                 235                 240

Glu Leu Ser Asp Gly Ser Leu Met Leu Asn Ser Arg Ala Ser Asp Gly
                245                 250                 255

Ser Gly Phe Arg Lys Val Ala His Ser Thr Asp Gly Gly Gln Thr Trp
            260                 265                 270

Ser Glu Pro Val Ser Asp Lys Asn Leu Pro Asp Ser Val Asp Asn Ala
            275                 280                 285

Gln Ile Ile Arg Ala Phe Pro Asn Ala Ala Pro Asp Asp Pro Arg Ala
    290                 295                 300
```

-continued

```
Lys Val Leu Leu Leu Ser His Ser Pro Asn Pro Arg Pro Trp Ser Arg
305                 310                 315                 320

Asp Arg Gly Thr Ile Ser Met Ser Cys Asp Asp Gly Ala Ser Trp Thr
                325                 330                 335

Thr Ser Lys Val Phe His Glu Pro Phe Val Gly Tyr Thr Thr Ile Ala
            340                 345                 350

Val Gln Ser Asp Gly Ser Ile Gly Leu Leu Ser Glu Asp Ala His Asn
        355                 360                 365

Gly Ala Asp Tyr Gly Gly Ile Trp Tyr Arg Asn Phe Thr Met Asn Trp
    370                 375                 380

Leu Gly Glu Gln Cys Gly Gln Lys Pro Ala Lys Arg Lys Lys Lys Gly
385                 390                 395                 400

Gly Lys Asn Gly Lys Asn Arg Arg Asn Arg Lys Lys Lys Asn Pro
                405                 410                 415
```

METHOD OF PROTEIN PURIFICATION FROM E.COLI

RELATED APPLICATION

This application is a continuation and claims priority to U.S. application Ser. No. 14/210,728, filed Mar. 14, 2014, which claims priority to U.S. Provisional Application Ser. No. 61/800,345, filed Mar. 15, 2013, the entire contents are which hereby incorporated by reference.

STATEMENT REGARDING FEDERALLY SPONSORED RESEARCH

The invention disclosed herein was made in part with Government funding, and the Government has certain rights in the invention. In particular, portions of the invention disclosed herein were funded, in part, under Contract No. N01-AI-60015C awarded by National Institutes of Health.

FIELD OF INVENTION

This disclosure relates generally to a novel method and reagents to obtain intracellular proteins from a cell culture.

BACKGROUND

The concerns surrounding large-scale purification of proteins are an increasingly important issue for the biotechnology industry. Numerous disorders have been the subject of protein or enzyme replacement therapy including, dystrophic epidermolysis bullosa, and lysosomal storage disorders such as Gaucher disease, Fabry disease and Pompe disease. The large scale protein production required to supply patients must be cost sensitive, have production efficiency and yield high quality product. The process of protein purification is lengthy in time, burdensome as well as costly. These disadvantages greatly affect the cost of protein replacement therapy and pose a formidable challenge to healthcare in general.

Protein production is mainly performed in cells, i.e., mammalian, bacterial or fungal engineered to produce the protein of interest by insertion of a recombinant plasmid containing the gene for that protein. Cells expressing the protein of interest are cultured in a complex growth medium, containing sugars, amino acids, and growth factors, usually supplied from preparations of animal serum. Purification requires separation of the desired protein from the mixture of compounds fed to the cells as well as from cellular debris in order to purity sufficient amounts in high quality for use as a human therapeutic Procedures for purification of proteins from cell debris are lengthy and complex. Multiple and repeated steps required to remove the protein of interest greatly compromises the final protein yield and quality. In many instances, the protein must be functional upon purification.

Recombinant proteins expressed in an intracellular compartment of a biological expression system are generally released from the expression system cells by mechanical disruption in cases where there is a cell wall. Such mechanical methods include homogenization, microfluidization, nitrogen burst, ultrasonic, and bead agitation methods. Other methods include the addition of enzymes to partially degrade cell wall components followed by osmotic agents to induce rupture and release of periplasm contents. These methods combining enzymatic digestion and chemical treatment are largely used for expressed proteins targeted to the periplasmic space in gram negative bacteria. Cells that have no cell wall may be disrupted by osmotic pressure without addition of enzymes, or complete by disruption of the cell membrane using detergents or organic solvents. Disruption methods may be used in combination for enhanced efficiency.

Most of the previous methods are suitable only for release of proteins from the periplasmic compartment, or result in complete disruption of the cell compartment. When the cell is completely disrupted, DNA may be released from sub-cellular compartments and cause formation of a highly viscous liquid. The DNA can be sheared or enzymatically degraded to reduce viscosity and enable handling the process fluid stream during larger scale productions. These steps are used successfully for production of pharmaceutical grade proteins; however, each process step increases the complexity, time and cost of manufacturing

SUMMARY OF THE INVENTION

The present disclosure provides novel methods and reagents related to the method to purify intracellular proteins of interest from bacterial cells, particularly $E.\ coli$, present in a culture media (i) without removal of the cells from the culture media, (ii) without using mechanical disruption of the cells or the use of enzymes to degrade cell wall; and (iii) without consolidating the population of cells to a concentrated pellet form.

The disclosed method is used to release intracellular recombinant proteins by the addition of a pre-determined combination of inorganic salts and detergents to permeabilize cells for the release of recombinant proteins without causing the total disruption of cells, thereby reducing the amount of DNA release and resulting increased viscosity.

The remaining cellular debris may be purified away from a soluble recombinant protein by a centrifugation step following selective precipitation.

The method may be accomplished by a series of steps involving the addition of the appropriate chemical reagents to the bioreactor after completion of cell culture, i.e., fermentation. These chemical reagents are added to the culture in a stepwise manner. The reagents are also added so as to achieve a particular concentration of that reagent. The method requires the presence of the chemical reagent in the solution for a defined amount of time.

The method does not require isolation of the cells from the cell culture. Further, it does not require removal of the growth media prior to addition of the reagents ("release reagents"). The method does not utilize mechanical disruption to lyse the cells.

In doing so, the method reduces the complexity, time and cost of manufacturing, while increasing the robustness due to reduced DNA release.

This document provides a method for releasing a protein of interest from a bacterial cell or fungal expressing the protein of interest. The method includes: (a) providing a culture of cells expressing a protein of interest (e.g., cells expressing the protein of interest and growth media in which the cells have been cultured); (b) contacting the culture of cells with an inorganic salt (e.g., by adding a composition comprising the inorganic salt to the culture); (c) holding the culture containing the added inorganic salt for at least 10 minutes; (d) contacting the culture containing the added inorganic salt with a chelating agent (e.g., by adding a composition comprising the chelating agent the culture); (e) holding the culture containing the added inorganic salt and the added chelating agent for at least 10 minutes; (f) optionally adjusting the pH of the culture containing the added inorganic salt and the added chelating agent to a pH between 4 and 9; (g) holding the culture containing the added inorganic salt and the added chelating agent for at least 15 minutes after pH adjustment; (h) contacting the culture containing the added inorganic salt and the added chelating agent with a detergent; (i) holding the culture containing the added inorganic salt, the added chelating agent and the added detergent for at least 1 hour; (j) optionally lowering the temperature of the culture containing the added inorganic salt, the added chelating agent and the added detergent; (k) contacting the culture containing the added inorganic salt, the added chelating agent and the added detergent with a precipitating agent; (l) holding the culture containing the added inorganic salt, the added chelating agent, the added detergent, and the added precipitating agent for at least 1 hour; and (m) subjecting the culture comprising the added inorganic salt, the added chelating agent, the added detergent and the added precipitating agent to a method to remove a substantial portion (e.g., at least 90%) of the cellular debris. The method does not include at least two steps selected from a group consisting of: (i) mechanical disruption of the cell, (ii) removing all or substantially all of the culture media prior to the additions, and (iii) addition of an enzyme that digests cell wall material. In some cases, the method does not include any of: (i) mechanical disruption of the cell, (ii) removing substantially all of the culture media, and (iii) addition of an enzyme that digests cell wall material. The above method can also include removing a portion or substantially all of the culture media.

In the above method where an inorganic salt is used, the inorganic salt can be sodium phosphate, ammonium sulfate, and sodium chloride. In the above method where a detergent is used, it can be Triton, SDS, CHAPS 3, Nonidet P40, n-Octylglucoside, and Tween-20. The method above also uses a mixture of two detergents that can be selected from Triton, SDS, CHAPS 3, Nonidet P40, n-Octylglucoside, and Tween-20. The method above that also uses a precipitating agent that can be PEI, and ammonium salt, and polyethylene glycol, TCA and ethanol.

I some cases the cell expressing the desired protein is $E.\ coli$. The above method uses a bacterial cell that is a gram negative bacteria. The desired protein is an intracellular protein (i.e., it is not secreted from the cell). The protein of interest can be DAS181.

In all the above methods, the step of holding the culture containing the inorganic salt occurs for at least 20 minutes. In all the above methods the step of holding the culture containing the inorganic salt and the chelating agent can be for at least 15 minutes is at least 30 minutes, 45 minutes, or 1 hour or between 30 min and 1 hour.

In all the above methods, the step of holding the culture containing the inorganic salt, the chelating agent and the detergent can take place for at least 1 hour, at least 30 minutes, 1 hours, 2 hours, 3 hours, 4 hours, 5 hours, 6 hours, 7 hours, 8 hours, hours 6 hours, 7 hours, 8 hours, 9 hours, 10 hours, 11 hours, 12 hours, or 5-13 hours. In all the above methods, the step of holding the culture containing the inorganic salt, the chelating agent, the detergent and the precipitating agent can take place for at least 1 hour, at least 30 minutes, 1 hours, 2 hours, 3 hours, 4 hours, 5 hours, 6 hours, 7 hours, 8 hours, hours 6 hours, 7 hours, 8 hours, 9 hours, 10 hours, 11 hours, 12 hours, or 5-13 hours.

The steps can take place when the mixture is at 25-35° C., preferably 30° C. The temperate of the mixture can be reduced below 25° C., e.g., between 25 and 20° C. or to between 21 and 23° C. prior to the addition of precipitating agent.

DESCRIPTION OF THE DRAWINGS

FIG. 3A and FIG. 3B depict the coomassie detection of proteins isolated from the homogenization protocol (FIG. 3A) and the detergent solubilization protocol (FIG. 3B). FIG. 3C and FIG. 3D depict the silver detection of proteins isolated from the homogenization protocol (FIG. 3C) and the detergent solubilization protocol (FIG. 3D). FIG. 3E is the SDS-PAGE comparison gel with silver detection (lanes 1-8 contain, Molecular Weight Marker, samples from the homogenization protocol (lanes 2-4), samples from the detergent solubilization protocol (lanes 5-7) and DAS 181 Ref Std 750-0406-002 (lane 8), respectively. In FIG. 3A, lanes 1-10 contain: the molecular weight marker, clarified homogenate, SP Flow-through, SP Eluate, HIC Eluate, Post HIC TFF, RPC Load, RPC Eluate, and DAS181 Ref Std 750-0406-002, respectively. In FIG. 3B, lanes 1-10 contain: Molecular Weight Marker, PEI Clarified Detergent, Detergent SP Load, Detergent SP Flow-through, Detergent SP Eluate, Detergent HIC Eluate, Detergent Post-HIC TFF, RPC Load, RPC Eluate and DAS181 Ref Std 750-0406-002, respectively. In FIG. 3C, lanes 1-10 contain: the Molecular Weight Marker, Clarified Homogenate, SP Flow-through, SP Eluate, HIC Eluate, Post HIC TFF, RPC Eluate, and DAS181 Ref Std 750-0406-002, respectively. In FIG. 3D, lanes 1-10 contain: Molecular Weight Marker, PEI Clarified Detergent, Detergent SP Load, Detergent SP Flow-through, Detergent SP Eluate, Detergent HIC Eluate, Detergent Post-HIC TFF, RPC Load, RPC Eluate and DAS 181 Ref Std 750-0406-002, respectively.

FIG. 5 A-F are analyses of protein for Runs A and B. FIGS. A-C are the coomassie stain, Western Blot and Silver Stain analyses of detergent solubilization yields of Run A, respectively. Lanes 1-10 for these analyses are as follows: MW Marker, SP Eluate (Ferm 20110523F2), HIC FT, UF/DF #1 Pool, Capto Adhere FT pH 7.7, Titrated Capto Adhere FT pH 5.0, Drug Substance and DAS181 Ref. Std, respectively. FIGS. D-F are the coomassie stain, Western Blot and Silver Stain of the detergent solubilization yields of Run B, respectively. Lanes 1-10 for these analyses are as follows: MW Marker, SP Eluate (Ferm 20110613F2), HIC FT, UF/DF #1 Pool, Capto Adhere FT pH 7.7, Titrated Capto Adhere FT pH 5.0, Drug Substance, and DAS181 Ref. Std. Lot 46-012, respectively.

DETAILED DESCRIPTION

Figure 1:
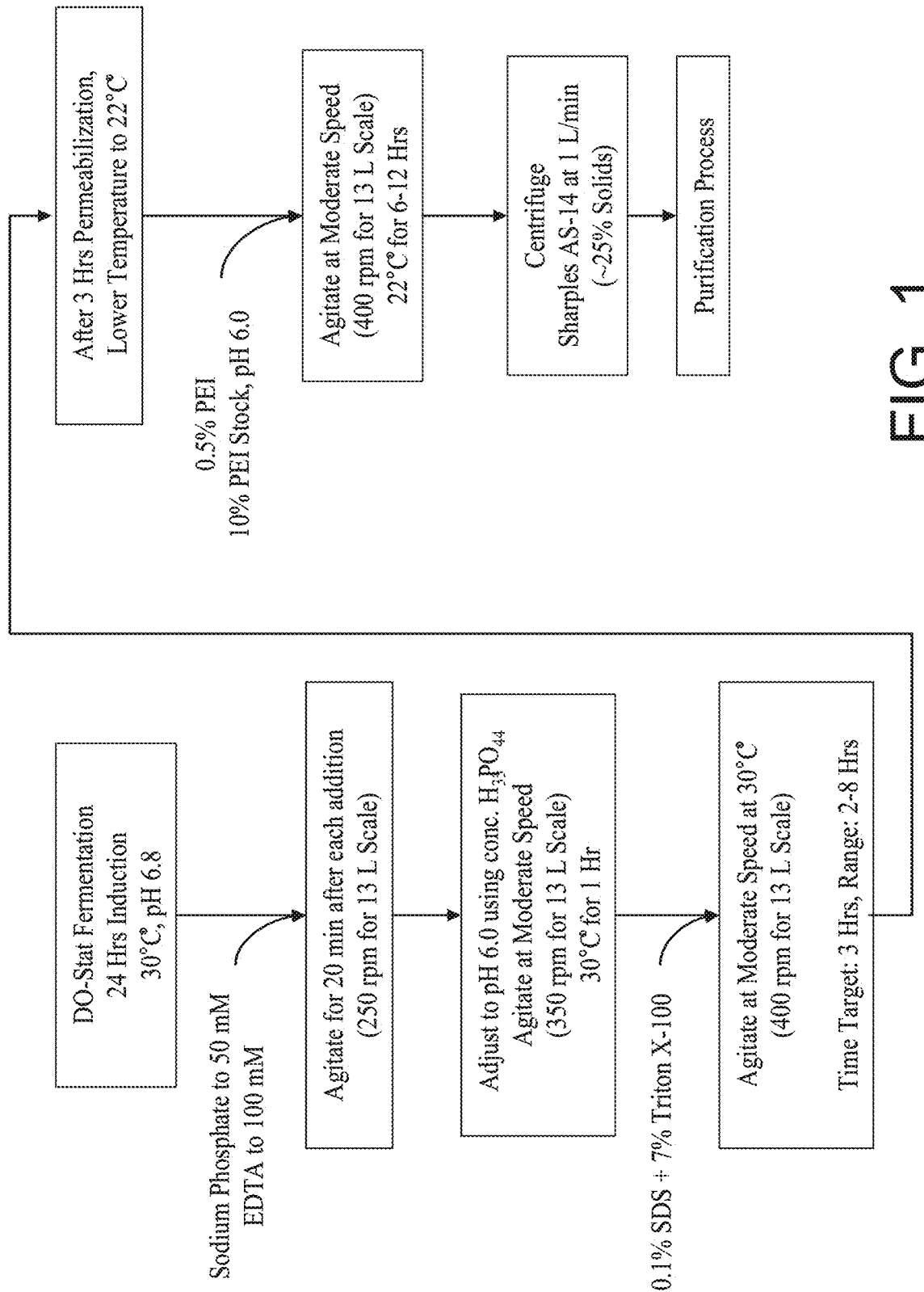
FIG. 1 is a flow chart of an embodiment the novel protein release protocol.

The methods described herein can be used generally to release an intracellular protein for from bacterial cells, particularly *E. coli*. The examples herein relate to release of DAS181 (Malakhov et al., *Antimicrob. Agents Chemother*, 1470-1479 (2006)) from *E coli*. DAS181 is a fusion protein containing the heparin (glysosaminoglycan, or GAG) binding domain from human amphiregulin fused via its N-terminus to the C-terminus of a catalytic domain of *Actinomyces Viscosus* (e.g., sequence of amino acids set forth in SEQ ID NO: 1 (no amino terminal methionine) and SEQ ID NO: 2 (including amino terminal methionine). The genetically engineered cells described herein contain one or more nucleic acids encoding the DAS181 protein. Cells suitable for in vivo production of DAS181 or for recombinant production of any of the polypeptides described herein can be of bacterial or fungal origin.

Overexpressing a protein in a cell (e.g., a bacterial cell) can be achieved using an expression vector. Expression vectors can be autonomous or integrative. A recombinant nucleic acid (e.g., one encoding DAS181) can be in introduced into the cell in the form of an expression vector such as a plasmid. The recombinant nucleic acid can be maintained extra chromosomally or it can be integrated into the chromosomal DNA. Expression vectors can contain selection marker genes encoding proteins required for cell viability under selected conditions (to permit detection and/or selection of those cells transformed with the desired nucleic acids. Expression vectors can also include an autonomous replication sequence (ARS).

Transformed cells (i.e., bacterial cells) can be selected for by using appropriate techniques including, but not limited to, culturing auxotrophic cells after transformation in the absence of the biochemical product required, selection for and detection of a new phenotype, or culturing in the presence of an antibiotic which is toxic to the yeast in the absence of a resistance gene contained in the transformants. Transformants can also be selected and/or verified by integration of the expression cassette into the genome, which can be assessed by, e.g., Southern blot or PCR analysis. Prior to introducing the vectors into a target cell of interest, the vectors can be grown (e.g., amplified) in bacterial cells such as *Escherichia coli* (*E. coli*) as described above. The vector DNA can be isolated from bacterial cells by any of the methods known in the art which result in the purification of vector DNA from the bacterial milieu. The purified vector DNA can be extracted extensively with phenol, chloroform, and ether, to ensure that no *E. coli* proteins are present in the plasmid DNA preparation, since these proteins can be toxic to mammalian cells.

Expression systems that can be used for small or large scale production of polypeptides include, without limitation, microorganisms such as bacteria (e.g., *E. coli*) transformed with recombinant bacteriophage DNA, plasmid DNA, or cosmid DNA expression vectors containing the nucleic acid molecules, and fungal (e.g., *S. cerevisiae*) transformed with recombinant fungal expression vectors containing the nucleic acid molecules.

In general, for in vivo production of a protein of interest by bacterial (e.g., *E. coli*) recombinant cells, the cells can be cultured in an aqueous nutrient medium comprising sources of assimilatable nitrogen and carbon, typically under submerged aerobic conditions (shaking culture, submerged culture, etc.). The aqueous medium can be maintained at a pH of 4.0-8.0 (e.g., 4.5, 5.0, 5.5, 6.0, or 7.5), using protein components in the medium, buffers incorporated into the medium or by external addition of acid or base as required. Suitable sources of carbon in the nutrient medium can include, for example, carbohydrates, lipids and organic acids such as glucose, sucrose, fructose, glycerol, starch, vegetable oils, petrochemical derived oils, succinate, formate and the like. Suitable sources of nitrogen can include, for example, yeast extract, Corn Steep Liquor, meat extract, peptone, vegetable meals, distillers solubles, dried yeast, and the like as well as inorganic nitrogen sources such as ammonium sulphate, ammonium phosphate, nitrate salts, urea, amino acids and the like.

Carbon and nitrogen sources, advantageously used in combination, need not be used in pure form because less pure materials, which contain traces of growth factors and considerable quantities of mineral nutrients, are also suitable for use. Desired mineral salts such as sodium or potassium phosphate, sodium or potassium chloride, magnesium salts, copper salts and the like can be added to the medium. An antifoam agent such as liquid paraffin or vegetable oils may be added in trace quantities as required but is not typically required.

Cultivation of recombinant cells (e.g., *E. coli* cells) expressing a protein of interest can be performed under conditions that promote optimal biomass and/or enzyme titer yields. Such conditions include, for example, batch, fed-batch or continuous culture. Further, changes to the parameters of the conditions can also promote optimal biomass and/or enzyme titer yields of the DAS181 protein. Such conditions include, for example, glycerol concentration in the culture media and high $pO_2$. For production of high amounts of biomass, submerged aerobic culture methods can be used, while smaller quantities can be cultured in shake flasks. For production in large tanks, a number of smaller inoculum tanks can be used to build the inoculum to a level high enough to minimize the lag time in the production vessel. The medium for production of the biocatalyst is generally sterilized (e.g., by autoclaving) prior to inoculation with the cells. Aeration and agitation of the culture can be achieved by mechanical means simultaneous addition of sterile air or by addition of air alone in a bubble reactor. A higher $pO_2$ (dissolved oxygen) can be used during cultivation in, for example, a bioreactor to promote optimal biomass. It can also be used to promote optimal active protein expression in the biomass culture. Implementation of such fermentation parameters, including a higher partial oxygen pressure and stepwise glycerol depletion, can result in an increased production of the protein in interest.

Method of Detergent Solubilization

In-Situ Detergent Permeabilization

Following sufficient culturing for the desired protein expression, the culture is harvested by stopping feed addition and airflow into the reactor, and by reducing the agitation speed 100 to 250 rpm. The temperature is set in the range of 15° C. to 45° C. to prepare for the permeabilization step. In some embodiments, the temperature may be set at 30° C. This is also referred to as the pre-treatment step in this disclosure. An inorganic salt (e.g., sodium phosphate, ammonium sulfate, and sodium chloride) can be added to a final concentration in the range of 10-100 mM. In some embodiments, the final concentration of inorganic salt is 50 mM. The solution is allowed to be mixed for at least 10 or at least 20 minutes. A chelating agent such as Ethylenediamine Tetraacetic Acid (EDTA) is added to a final concentration in the range of 50-200 mM and mixed for at least 10 minutes or at least 20 minutes. In some embodiments, EDTA is added to a final concentration of 100 mM (e.g., 50 nM-250 nM). The pH can subsequently adjusted to 5.0-6.0 (e.g., using phosphoric acid). In some embodiments, the pH is adjusted to 6. The material is incubated for at least 10 minutes (e.g., amount of time in the range of 30 minutes to 180 minutes or longer) with mixing (e.g., at an mixing speed of 400-450 rpm). In some embodiments of the method, the material is incubated for 60 minutes. A detergent (e.g., Triton, SDS, CHAPS 3, Nonidet P40, n-Octylglucoside, and Tween-20) or a combination of detergents, e.g., Sodium Dodecyl Sulfate (SDS) Triton-X 100, is added to the mixture. The Triton-X 100 may be used in the range of 2-15% together in combination with 0.01-1% SDS. In some embodiments, 10% SDS solution is subsequently added to a final concentration of 0.1% and Triton X-100 is added simultaneously to a final concentration of 7%. The solution is mixed can be mixed for an amount of time in the range of 1-5 hours at a moderate speed at a temperature in the range of 15-45° C. In some embodiments, the solution is mixed for 3 hours at a moderate speed at 30° C.

Clarification

Following incubation in the detergent combination, the mixture temperature is reduced to 22° C. Ten percent (10%) PEI, pH 6.0 stock solution is subsequently added to a final concentration of 0.5%. The solution can be mixed for the amount of time in the range of 6-24 hours at 22° C. In some embodiments, the solution is mixed for 6-12 hours at 22° C. In another embodiment of the method, the solution is mixed for a target of 6-8 hours at 22° C. The mixture is subsequently clarified by continuous flow centrifugation using Sharples AS-14 (feedflow rate: 1 L/min). The turbidity (OD600 nm) of the mixture is measured at T=0. The mixture can optionally be held at ambient temperature overnight prior to starting the protein purification process.

Following the above detergent solubilization methodology, products may be subject to further purification.

EXAMPLES

The invention is further described in the following examples, which do not limit the scope of the invention described in the claims.

The invention is a novel protein purification protocol that is performed without the requirement for the method of mechanical disruption of the cell or enzymatic degradation of the cell wall by exogenously added enzyme. It is also completed without the requirement of the isolation of the cells from the cell culture and further, does not have the requirement of removal of the cells from the culture medium.

The present novel solubilization protocol was optimized to yield high quality and stable protein of interest, DAS 181. The optimization of this novel protein purification is defined herein. The present protocol is also one that has benefits over the common mode of protein purification known in the art, namely homogenization. The quality, stability and integrity of the protein of interest, DAS181, upon purification via homogenization is compared to that via the novel solubilization protocol. The present protein purification protocol utilizes reagents at specified concentrations for a specified window of time. The optimization of these parameters is discussed below.

Example 1

Figure 2:
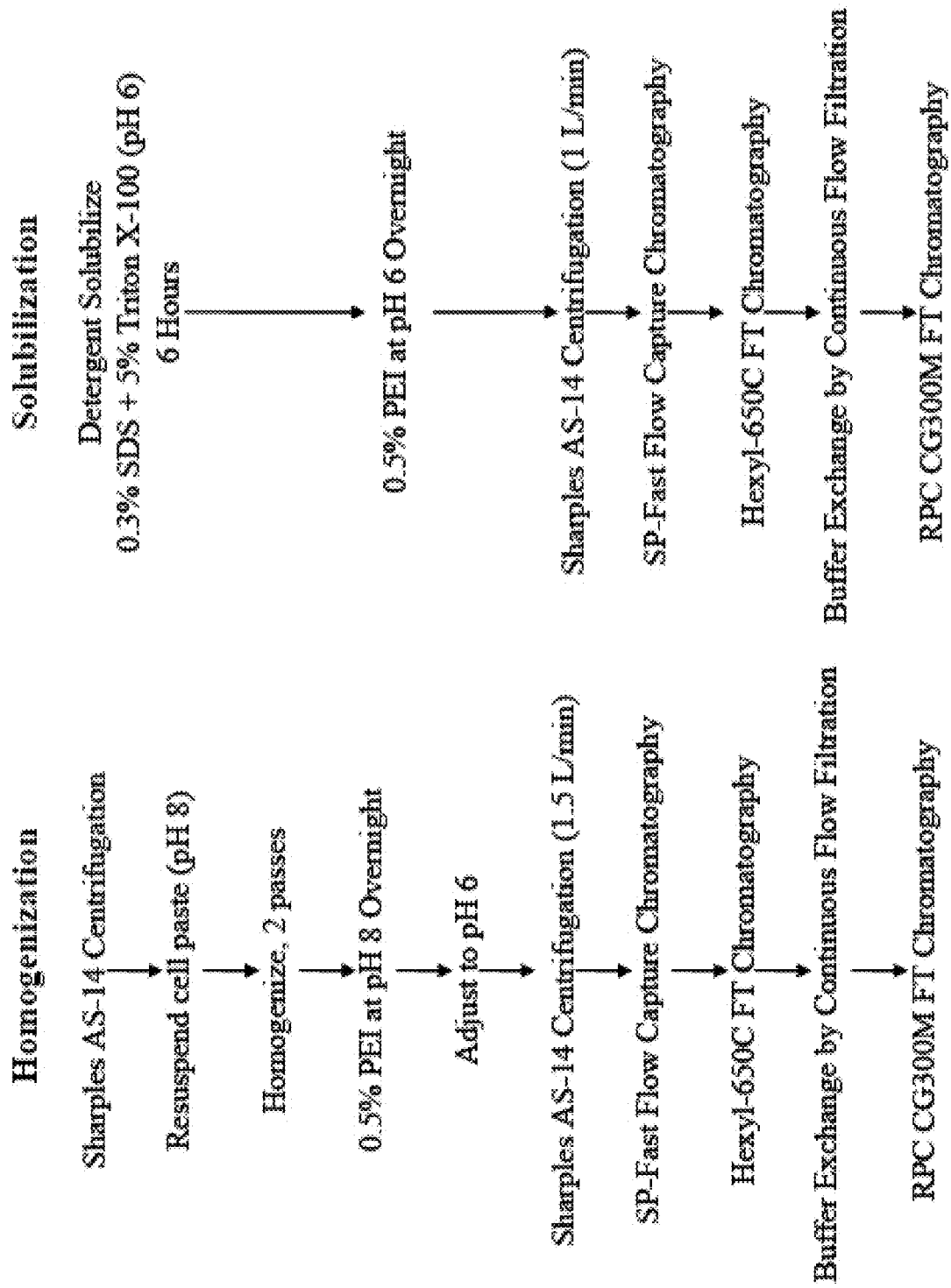
FIG. 2 is a comparison of the protein release method requiring homogenization lysis as compared to the novel protein release method ("detergent solubilization").

Protein Yield and Quality Resulting from Homogenization as Compared to Detergent Solubilization Extensive investigation was performed to optimize solubilization for in situ release of the protein of interest, DAS181, from cells as a streamlined alternative to protocols involving mechanical homogenization. Solubilization as compared to homogenization would reduce process time by allowing the release of DAS181 from cells without the steps of cell isolation, cell washing, resuspension, and homogenization. The details of Example 1 describe the methodology of solubilization as compared to that of homogenization and the subsequent results regarding protein yield as well as the quality of the purified protein. Flow charts depicting the methods of both solubilization and homogenization are presented in FIG. 2.

Method

Fermentations 20100201 F2 (F2) and 20100201 F3 (F3) were harvested after 24 hours of induction. The fermentations were pooled and split into two aliquots. Each aliquot was subject to either the solubilization method or the homogenization method going forward.

Preparation via the homogenization method: One aliquot (A) was centrifuged to remove the culture media. The pelleted cells were suspended in a buffer comprising 50 mM potassium phosphate and 200 mM NaCl, pH 8, and subsequently subject to two passes of homogenization at 15,000 psi on ice. The homogenate was then held at ambient temperature until further processing. The homogenate was subsequently treated with polyethyleneimine (PEI; stock 10% PEI, pH 8) to a final concentration of 0.5% and held at ambient temperature.

Preparation via the solubilization method: The second aliquot (B) was returned, as is, to the incubator for detergent solubilization at 30° C. Dibasic sodium phosphate heptahydrate and 1M EDTA (free acid at pH 8.7) was added to a final concentration of 50 mM, and 100 mM, respectively, under slow agitation. The pH was adjusted to 6.0 with 50% HCl and agitation was increased. The mixture was allowed to incubate for one hour prior to the addition of SDS and Triton X-100 to a final concentration of 0.3% and 5%, respectively. After 6 hours of detergent solubilization, the temperature of the solubilysate was reduced to 22° C., after which 10% PEI, pH 6 was added to a final concentration of 0.5%.

Going forward, both aliquots were treated equally. Aliquot A and B were incubated overnight while stirring. The homogenate was subsequently titrated to pH 6 using 50% HCl and allowed to shake for approximately 5 hours. Both aliquots were centrifuged and the supernatants filtered using further purification methods. The Clarified Detergent Solubilized DAS181 was diluted 1:1 with H2O and subject to additional purification methods. The homogenate was purified without the load dilution of the product of the further purification. Samples at each step were subject to measurement of OD600 nm and DTM CEX-HPLC to deduce yield and quality.

The DAS181 reference material is utilized as the standard for the assays below. Das181 reference material was purified using conventional homogenous protein purification method. The purified DAS181 is present in its active form.

Results

Turbidity of the centrifuged lysates following PEI treatment was determined before and after further purification. After continuous flow centrifugation, both lysates were found to be similar in turbidity with an OD600 nm of approximately 0.9. Following further purification, the turbidity of clarified homogenate was observed to be 0.1, while that of the clarified detergent material was 0.2. The reduced turbidity observed in the homogenate material was attributed to the PEI step performed at pH 8 as compared to pH 6 as in the detergent step of the solubilization method. In addition, as the homogenate material requires titration to pH 6 prior to centrifugation, the material was less stable over time. Clarified homogenate material held at RT and 4° C. increased in turbidity from 0.1 to 0.2 after 24 hours, while the turbidity of the clarified detergent material remained unchanged.

Yield at each process step was remarkably similar for both the lysis methods as shown in Table 1. The detergent solubilization step resulted in 83% of the total cellular protein amount being released whereas the homogenization step yielded 92%. Loss, however, was observed in the pre-homogenization cell centrifugation step. The yield, therefore, from fermentation to homogenization was 85%. The yield following PEI precipitation and each column step for the homogenate was similar. The overall yield for homogenization was 48%, while the yield for detergent solubilization was 44%.

TABLE 1

Comparison of protein yield from homogenization and new solubilization method

|  | Homogenization | | Solubilization | |
| --- | --- | --- | --- | --- |
| Process Intermediate | Step Yield | Total Yield | Step Yield | Total Yield |
| Harvest | 100.0% | 100.0% | 100.0% | 100.0% |
| Cell Pellet | 92.8% | 92.8% | | |
| Lysate | 91.7% | 85.1% | 83.3% | 83.3% |
| PEI Clarified Lysate | 89.6% | 76.3% | 90.5% | 75.3% |
| Filtered Lysate | 97.8% | 74.6% | 97.2% | 73.2% |
| SP Load | 100.0% | 74.6% | 95.0% | 69.6% |

TABLE 1-continued

Comparison of protein yield from homogenization and new solubilization method

|  | Homogenization | | Solubilization | |
| --- | --- | --- | --- | --- |
| Process Intermediate | Step Yield | Total Yield | Step Yield | Total Yield |
| SP Flow -through | 0.0% | 0.0% | 0.0% | 0.0% |
| SP Eluate | 107.6% | 80.3% | 107.8% | 75.0% |
| HIC FT Pool | 86.3% | 69.3% | 86.0% | 64.5% |
| Post-HIC TFF | 98.4% | 65.0% | 96.3% | 59.8% |
| RPC FT Pool | 90.2% | 48.3% | 75.0% | 43.7% |

Further purification was carried out and a summary of the product quality results is shown in Table 2. It was shown that the final product of homogenization and detergent solubilization is 99.9% and 99.8% monomer, respectively. The purity of the homogenate was 97.9%, while the purity of the detergent pool was 98.4%. Further purification showed that the homogenate RT FT pool was 6.5% peak F, 12.6 deamidated (peak C), and 81.0% main peak (peak A). The detergent pool was 7.3% peak F, 8.2% deamidated (peak C), and 84.5% main peak (peak A). The difference in deamidation is likely to be a result of the detergent process occurring at pH 6, whereas homogenization occurs at pH 8.

TABLE 2

DAS181 quality summary comparison between homogenization and thr new method 'solubilization'

|  |  | Homogenate | | | Solubilysate | | |
| --- | --- | --- | --- | --- | --- | --- | --- |
|  |  | SP Eluate | HIC FT | RP FT | SP Eluate | HIC FT | RPFT |
| Further protein purification methods: | 1 | 6.2% | 6.1% | 6.5% | 6.2% | 6.5% | 7.3% |
|  | 2 | 11.4% | 12.0% | 12.6% | 6.9% | 7.5% | 8.2% |
|  | 3 | 82.4% | 81.9% | 81.0% | 86.9% | 86.0% | 84.5% |
|  | 4 | 95.1% | 96.4% | 97.9% | 95.9% | 97.7% | 98.4% |
|  | 5 | 97.5% | 98.8% | 99.9% | 97.8% | 99.4% | 99.8% |
|  | 6 | 53800.0 | 1700.0 | 227.0 | 25700.0 | 39.0 | BLQ |

Analysis using further purification was also performed on the column fractions from each lysis method and is summarized in Table 2. The homogenate SP eluate contained nearly twice the amount of HCP than the detergent SP eluate. The homogenate following further purification contained over 40-fold the amount of HCP. The homogenate following further purification contained 227 ng/mg HCP and ≤16 ng/mg (BLQ), respectively.

Figure 3A:
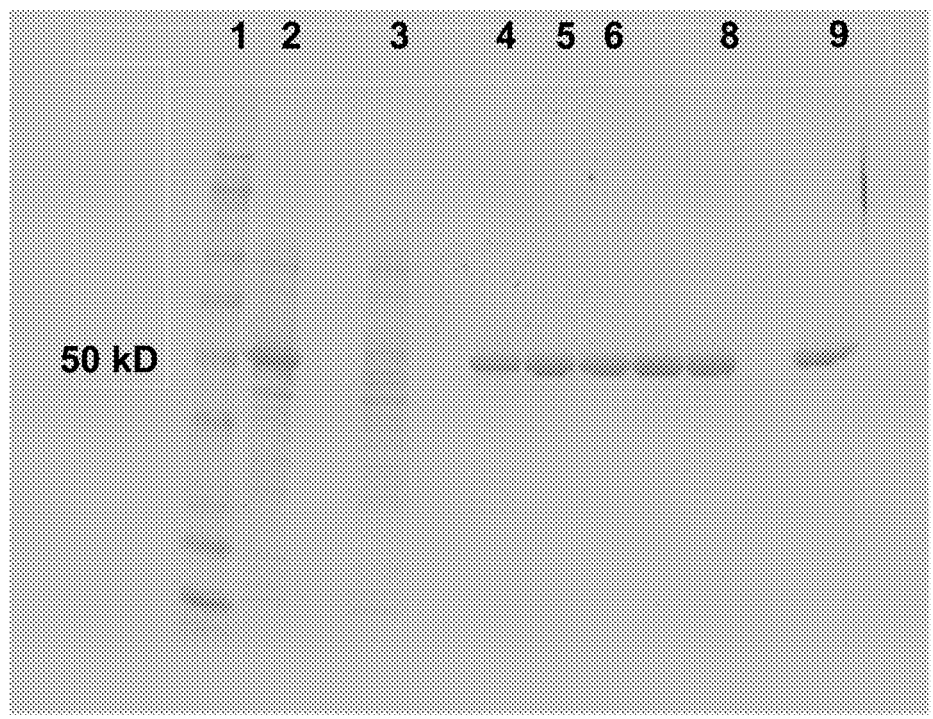
FIG. 3A-3E are the SDS PAGE analyses of the homogenization lysis protocol and the detergent solubilization protocol.
Figure 3B:
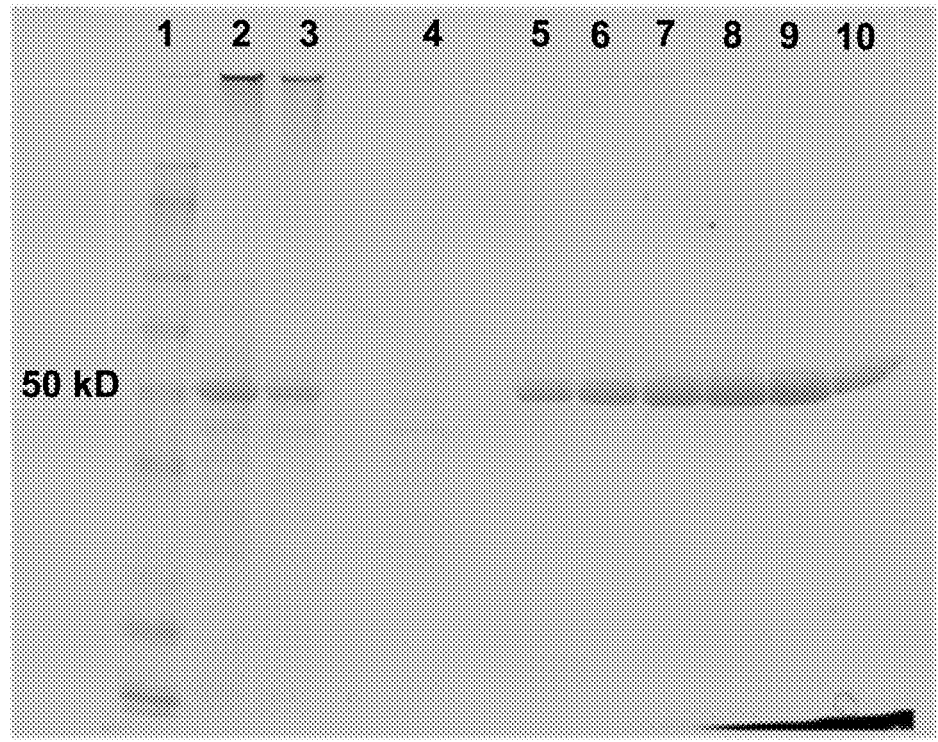
Figure 3C:
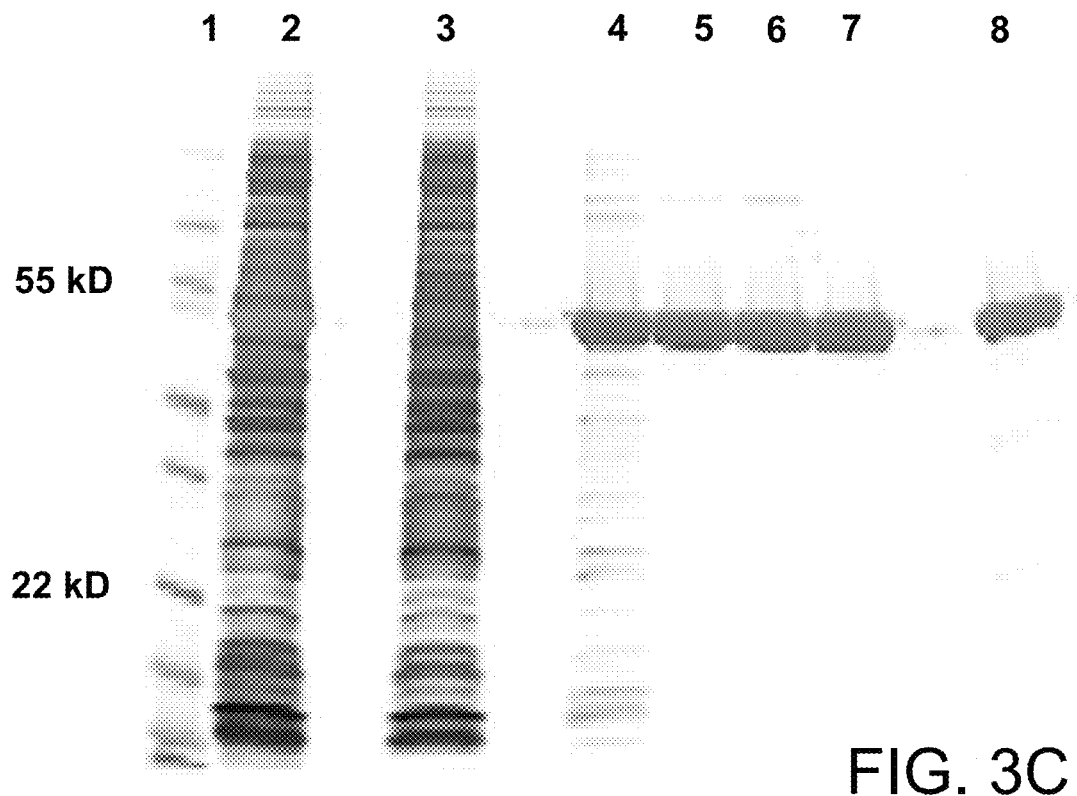
Figure 3D:
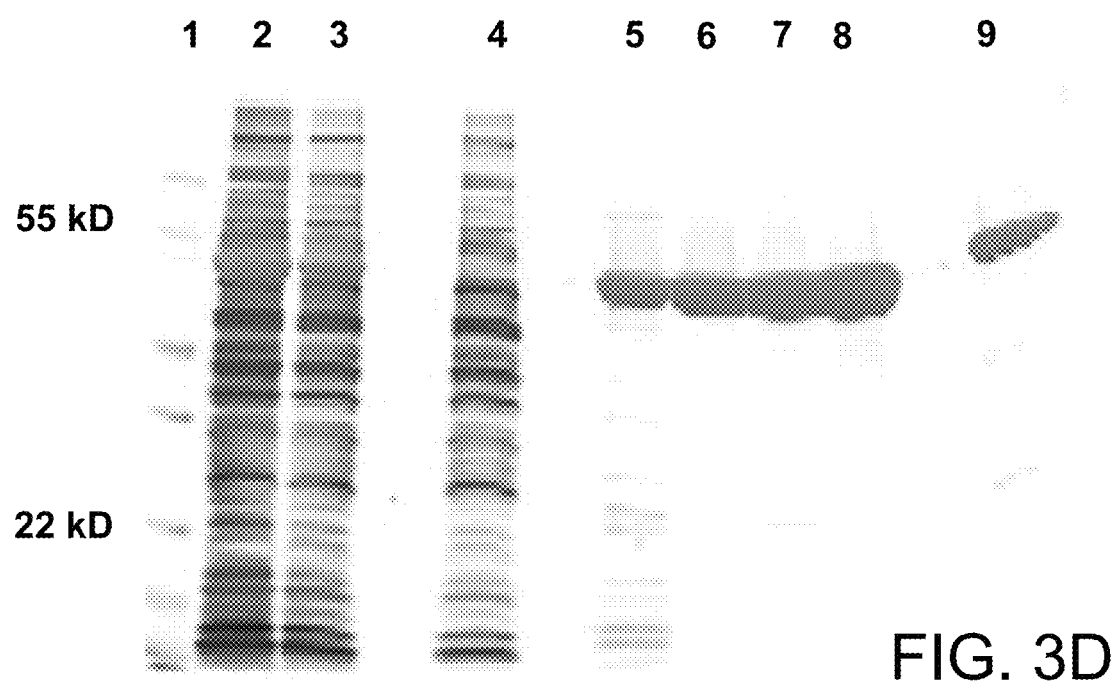
Figure 3E:
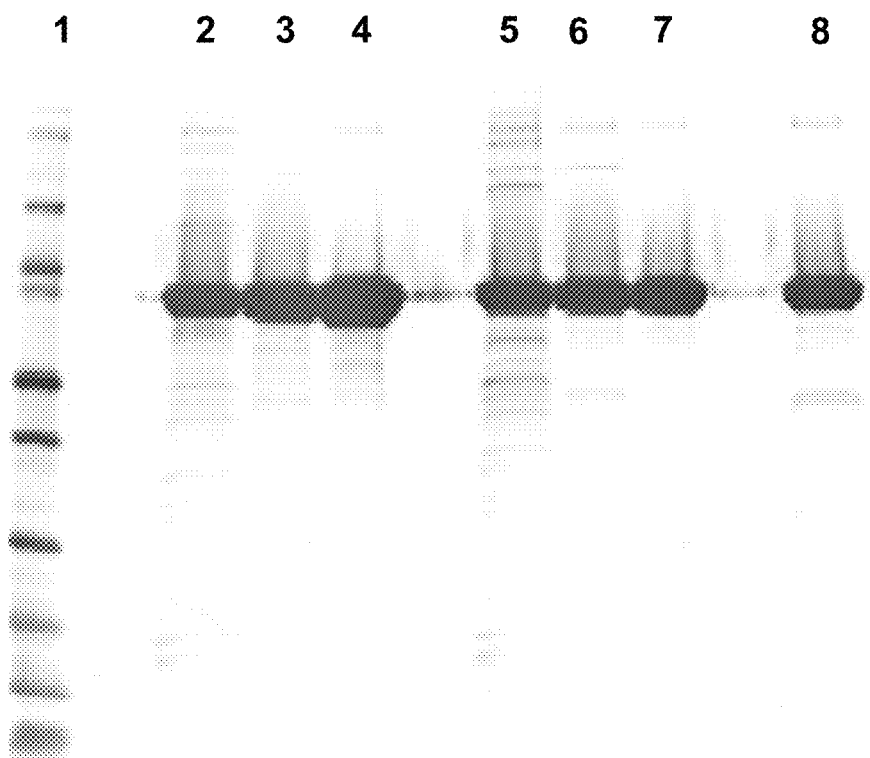

SDS-PAGE analysis indicated that the SP eluate produced from homogenization appeared slightly less pure than the detergent SP eluate (FIGS. 3A-3C). Overall, the samples produced from both lysis methods were similar. The final pools from the homogenization and detergent solubilization were consistent with the DAS181 reference standard present in Lane 9, 10 and 8 of FIGS. 3A, B and C, respectively.

It was concluded that the overall yield and product quality resulting from the detergent solubilization method and homogenization was comparable with the exception of the presence of host cell impurities in the lysate resulting from the homogenization process. These observations suggested that reduced processing time, enhanced process robustness, and a possible reduction in host cell impurities suggests that detergent solubilization is a viable alternative to homogenization for protein purification. These results justified the further testing and optimization of the detergent solubilization method.

Example 2

Optimization of Detergent Solubilization for Protein Expression and Purification Optimization of the novel detergent solubilization protocol was to ensure DAS181 drug substance purity as adequate and reproducible. The cleaning of the SP Capture column was made more effective with the use of a chaotropic agent, guanidine, in place of NaCl to ensure sufficient regeneration. Further, DAS181 recovery in the SP eluate was improved by increasing the dilution of the centrifugation supernatant prior to loading the sepharose resin. Hydrophobic interaction chromatography with Hexyl-650C resin was further optimized with an increase in loading capacity. The filtration and polishing steps were replaced with a single chromatography operation using a multimodal strong anion exchanger resin.

Method

Fermentation samples 20110523F2 and 20110613F2 were harvested after a 24 hour induction. Agitation was set to 250 rpm. Dibasic sodium phosphate heptahydrate and 1 M EDTA free acid at pH 8.7 was added to a final concentration of 50 mM and 100 mM. Agitation was increased to 350 rpm and the pH adjusted to 6.0 by the addition of phosphoric acid. The mixture was incubated for one hour prior to an increase in agitation to 400 rpm and the addition of SDS and Triton X-100 to a final concentration of 0.1% and 7%, respectively. Three hours following detergent permeabilization, the temperature of the permeabilysate was reduced to 22° C. Ten percent (10%) PEI, pH 6 was added to a final concentration of 0.5%. The materials were incubated for 6 hours before separation. The resulting supernatant was filtered using further purification methods. The clarified detergent permeabilysate was diluted by 125% volume to a final 2 M urea concentration.

Results

Figure 4:
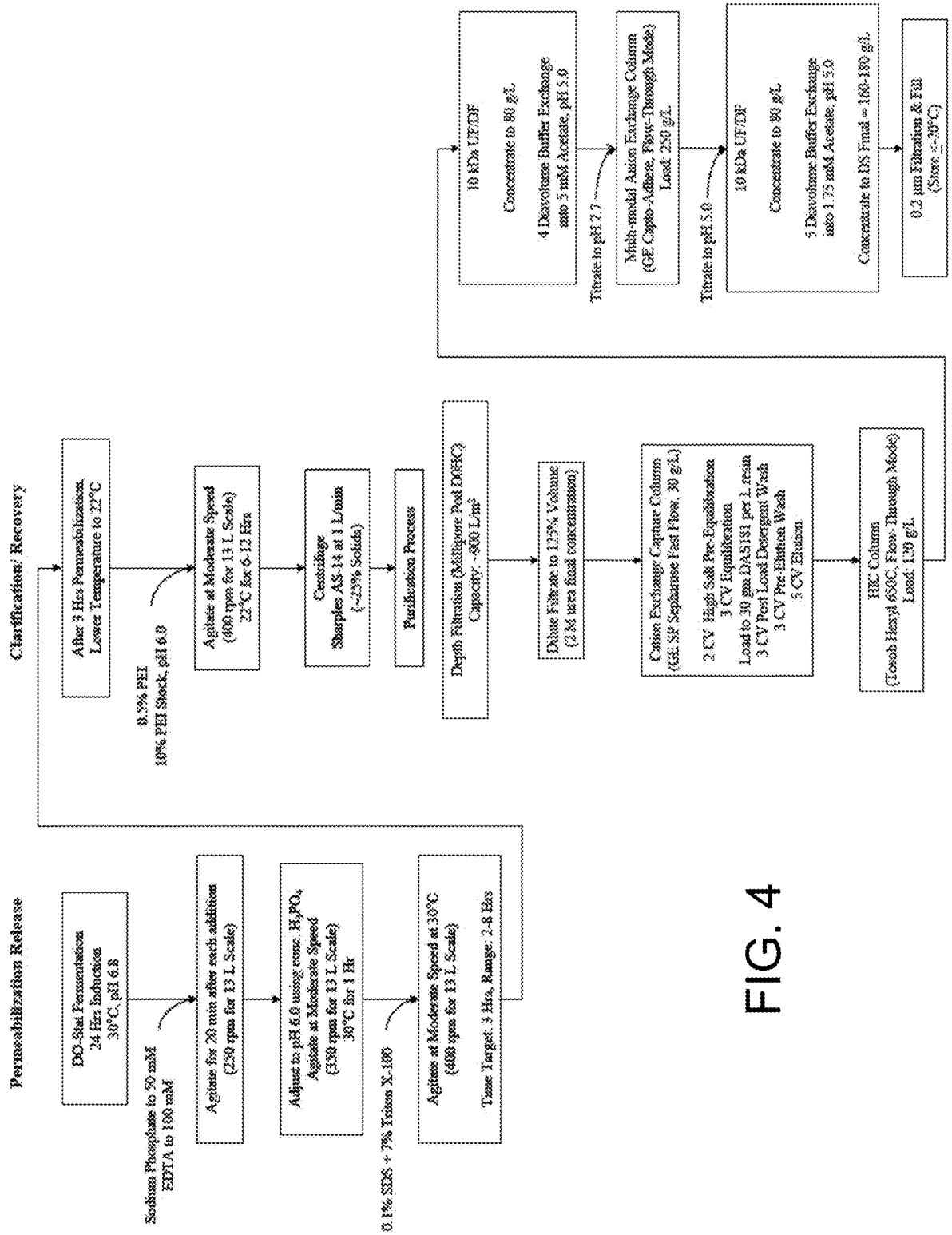
FIG. 4 is the flow chart of the optimized method of detergent solubilization and the steps of protein purification.
Figure 6A:
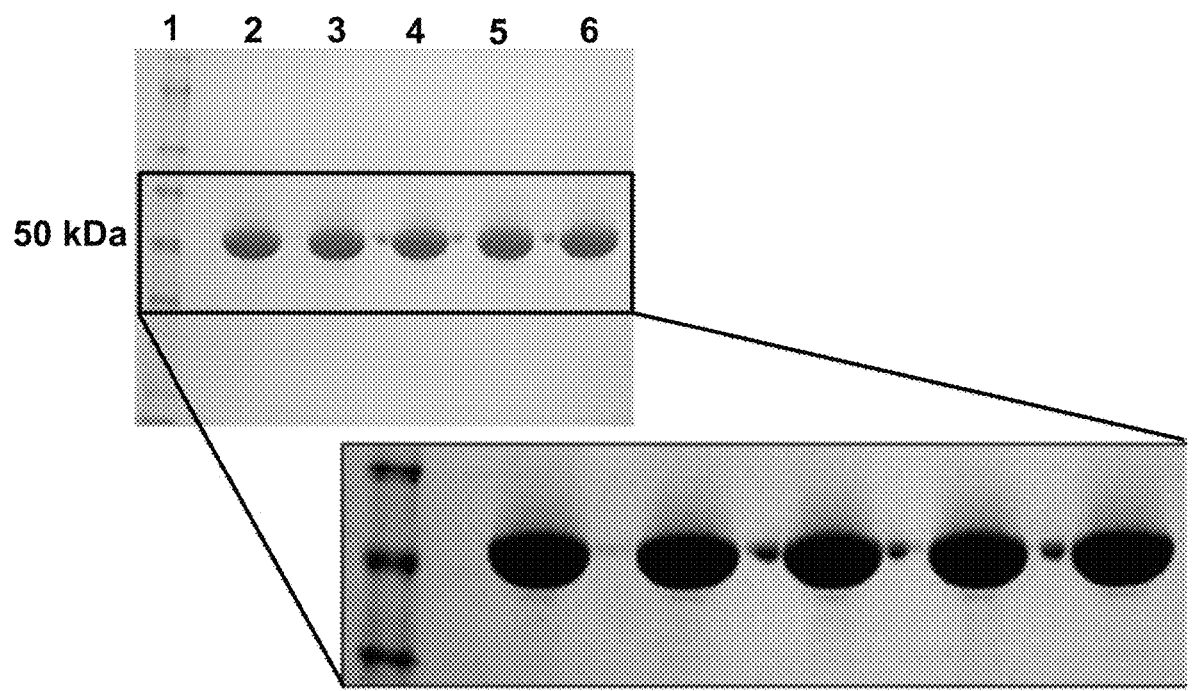
FIGS. 6 A and 6B are the SDS-PAGE analyses of DAS181 purity. Shown in FIG. 4A: lane is 1 MW Marker, lane 2 is Drug Substance Ferm 20110523F2, lanes 4 & 5 are Drug Substance Ferm 20110613F2, and lane 6 is DAS181 Phase 2 Ref. Std. Lot 46-012. Shown in FIG. 4B are different concentrations of the protein: 8-20 μg.
Figure 6B:
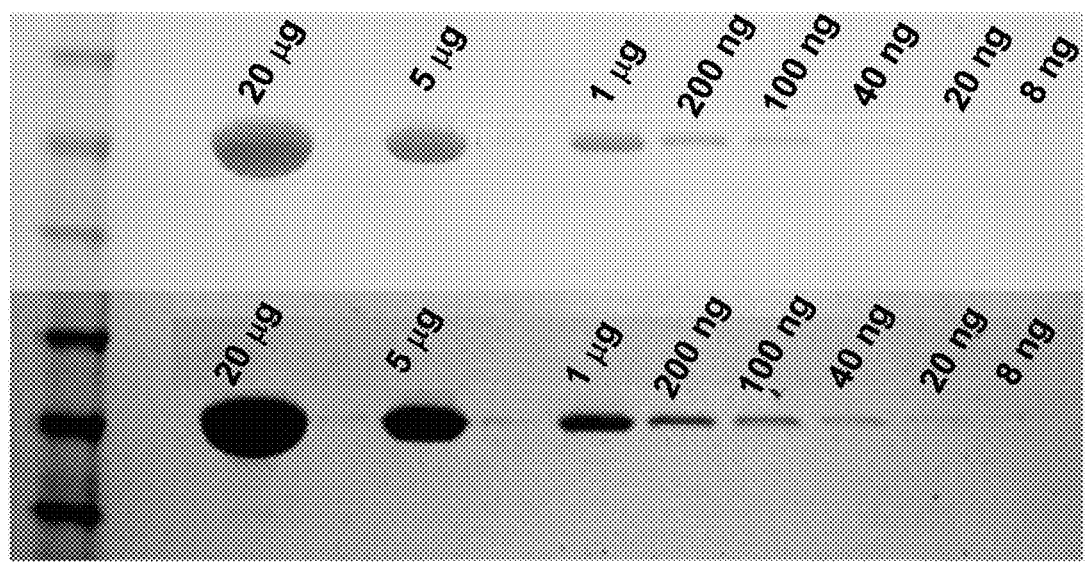
Figure 7A:
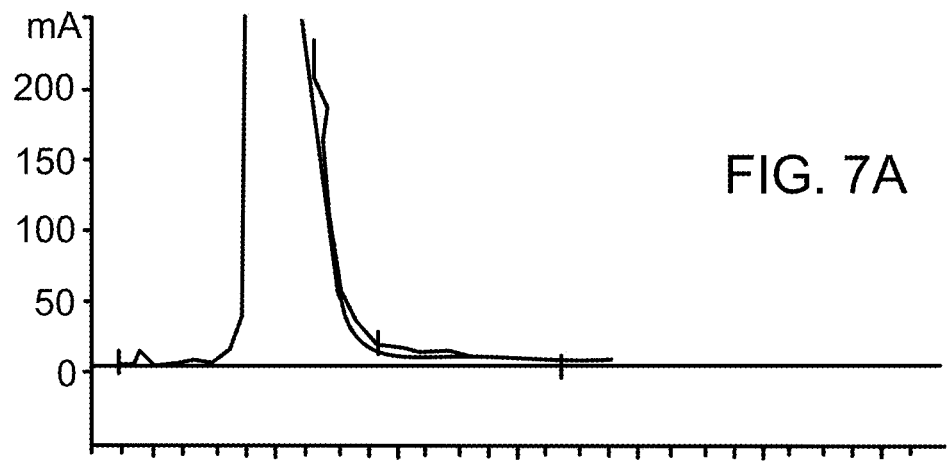
FIGS. 7A-7C show the RP-HPLC comparison of DAS 181 from: the integrated Run A, integrated Run B and the DAS reference standard
Figure 7B:
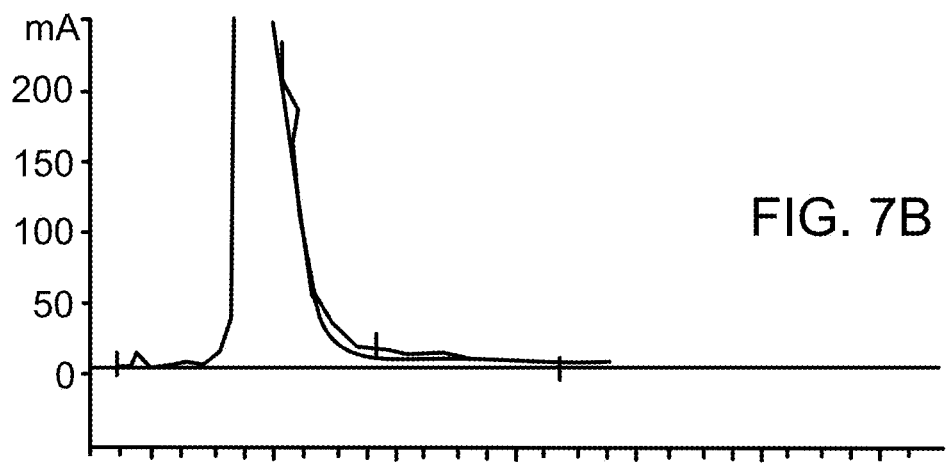
Figure 7C:
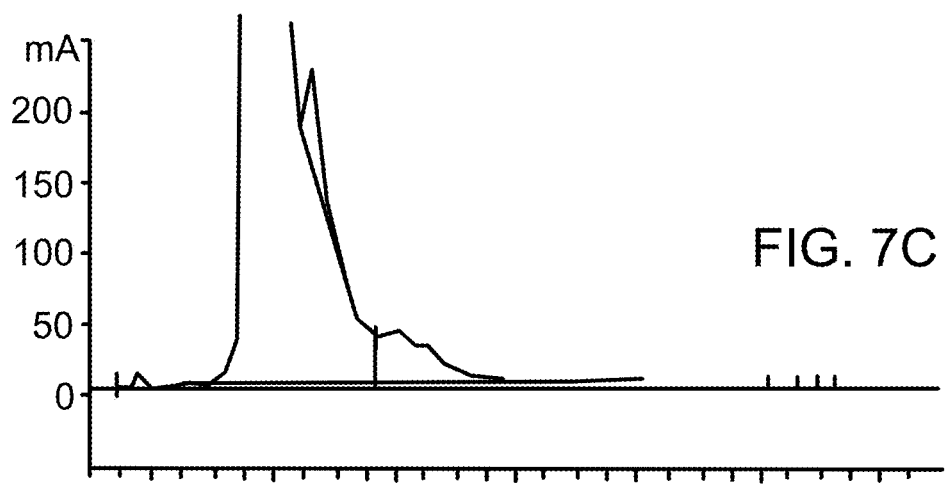

The final optimized recovery and purification processes are summarized FIG. 4. Two separate runs (Run A and Run B) of the novel detergent protocol were conducted in parallel and analyzed to deduce optimization of the protocol. SDS-PAGE with detection by Coomassie Blue, silver stain, and western blot analysis of purification intermediates from Run A (FIGS. 5A-5C) and Run B (FIGS. 5D-5F) showed stepwise increases in purity as purification proceeded. The final DAS181 drug substance purified from Runs A and B was comparable to the DAS181 reference standard detected by SDS-PAGE with Coomassie Blue. Silver stain detection however, revealed several lightly stained bands below the major band from samples of Runs A and B, signifying impurities. Conversely, Runs A and B had lower amounts of high molecular weight impurities than the reference standard. None of these bands were visible by Coomassie stain detection. Increasing the protein load for SDS-PAGE/Coomassie blue analysis (FIG. 6A) revealed that the drug substance from Run A and B were comparable to the reference standard. One major DAS181 band near 50 kDa was revealed whereas contrast-enhanced close-up revealed a minor band immediately below the major band for each loaded sample. This is likely an artifact of overloading the gel. A separate gel loaded with various quantities of reference standard (8 ng to 20 µg) demonstrated that SDS PAGE with colloidal blue stain could detect protein loads as low as 20 ng (FIG. 6B). Lanes loaded with 20 µg of drug substance from Run A and B showed no other visible bands with colloidal blue detection (FIG. 5). Therefore, the minor impurity bands detected in the drug substance lanes using silver stain accounted for less than 0.1% of the sample load (FIG. 5A-F), because bands that reached a 20 ng level would have been visualized by the colloidal Coomassie blue stain.

Aggregation analysis following further purification revealed that the drug substance from Runs A and B to be 99.8% and 99.9% monomer, respectively (Table 3).

TABLE 3

Analysis Comparison of products from alternative further purification

| | SEC-HPLC (% Monomer) | |
|---|---|---|
| Sample | Run #3 20110523F2 | Run #4 20110613F2 |
| SP Eluate | 99.6% | 99.7% |
| HIC FT | 99.8% | 99.8% |
| UF/DF #1 Pool | 99.7% | 99.8% |
| Capto Adhere FT pH 7.7 | 99.7% | 99.7% |
| Titrated Capto Adhere FT pH 5.0 | 99.8% | 99.9% |
| Drug Substance | 99.8% | 99.9% |

Purity analysis by further purification determined that the final drug substance from Runs A and B were 97.1% and 96.7% pure, respectively (Table 4).

TABLE 4

Analysis Comparison of products from alternative further purification

| | RP-HPLC (% Purity) | |
|---|---|---|
| Sample | Run #3 20110523F2 | Run #4 20110613F2 |
| SP Eluate | 94.5% | 94.5% |
| HIC FT | 94.8% | 93.4% |
| UF/DF #1 Pool | 93.9% | 93.9% |
| Capto Adhere FT pH 7.7 | 97.8% | 96.8% |
| Titrated Capto Adhere FT pH 5.0 | 97.6% | 96.6% |
| Drug Substance | 97.1% | 96.7% |
| DAS181 Phase 2 Ref. Std. Lot 46-012 | 94.2% | 94.5% |

The optimized process parameters used for Runs A and B resulted in a reduced peak area and quantity samples from further purification impurity peaks (FIG. 7A-E). Additionally, the shoulder off of the main DAS181 peak for the drug substance sample from run #1 to #4 was less pronounced than in the reference standard.

Figure 8A:
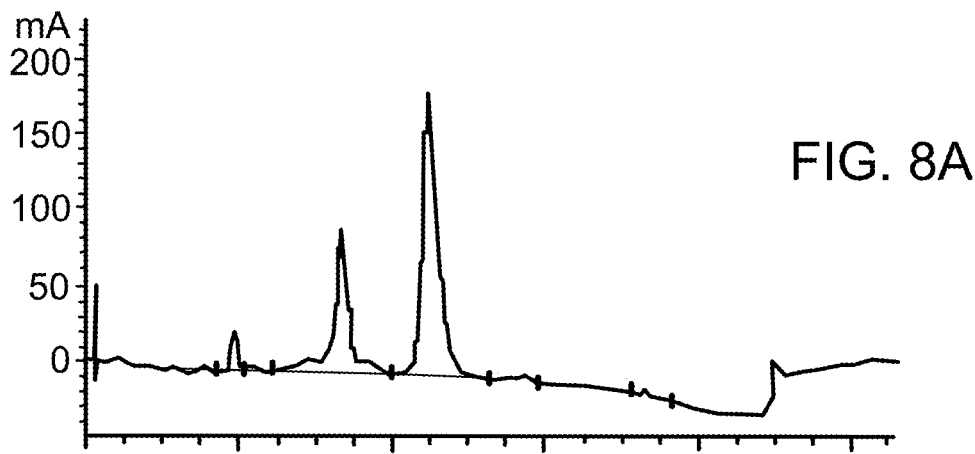
FIG. 8A-8C show the CEX-HPLC comparison of DAS181 from: integrated run A, integrated run B, and the DAS reference.
Figure 8B:
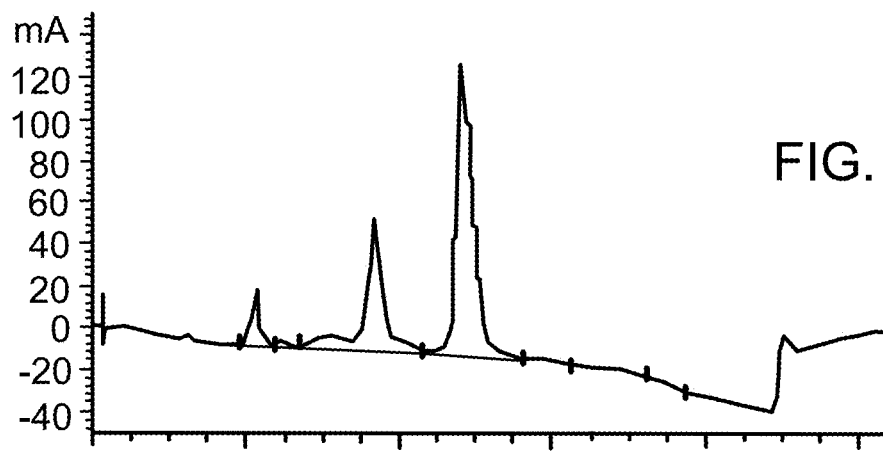
Figure 8C:
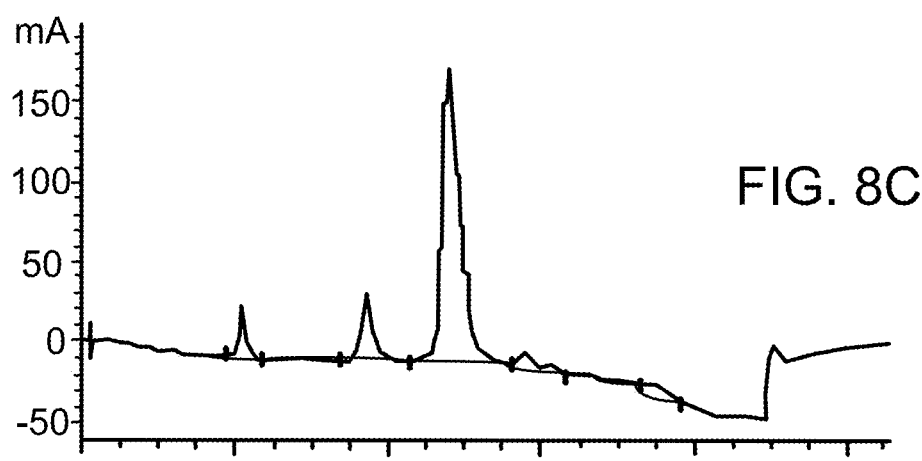

Analysis of DAS181 purity and variants obtained by further purification methods showed comparable chromatogram profiles of the final drug substance from bench-scale integrated Runs A and B to the DAS181 reference standard (FIG. 8), except for a difference in deamidation. An increase in deamidated DAS181 (peak C) was observed in the drug substances from Runs A and B (29.6±2.4%, compared to the reference standard at 13.2±0.1%). A corresponding decrease in DAS181 (peak A) was also observed. Peak A was determined to be 62.3% and 65.4% from Runs A and B, respectively (Table 5).

TABLE 5

CEX-HPLC Analysis Comparison
CEX-HPLC (% Peak Area)

| Sample | A | C | F | 1 | 4 |
|---|---|---|---|---|---|
| Run #3 Ferm 20110523F2 | | | | | |
| SP Eluate | 76.7% | 17.2% | 3.0% | 1.8% | 1.3% |
| HIC FT | 75.9% | 17.9% | 3.0% | 1.8% | 1.3% |
| UF/DF #1 Pool | 76.7% | 17.3% | 3.0% | 1.8% | 1.2% |
| Capto Adhere FT pH 7.7 | 60.9% | 33.5% | 3.4% | 1.4% | 0.8% |
| Titrated Capto Adhere FT pH 5.0 | 63.7% | 30.8% | 3.2% | 1.6% | 0.8% |
| Drug Substance | 62.3% | 31.9% | 3.3% | 1.6% | 0.9% |
| DAS181 Phase 2 Ref. Std. Lot 46-012 | 75.1% | 13.3% | 5.9% | 4.5% | 1.1% |
| Run #4 Ferm 20110613F2 | | | | | |
| SP Eluate | 75.8% | 17.4% | 5.2% | 0.7% | 0.9% |
| HIC FT | 76.1% | 16.6% | 5.3% | 1.0% | 0.9% |
| UF/DF #1 Pool | 76.6% | 16.3% | 5.3% | 1.0% | 0.8% |
| Capto Adhere FT pH 7.7 | 64.0% | 28.6% | 5.7% | 1.1% | 0.7% |
| Titrated Capto Adhere FT pH 5.0 | 63.0% | 26.5% | 5.4% | 1.1% | 4.1% |
| Drug Substance | 65.4% | 27.2% | 5.7% | 1.2% | 0.5% |
| DAS181 Phase 2 Ref. Std. Lot 46-012 | 75.9% | 13.1% | 6.1% | 4.1% | 0.8% |
| DAS181 Phase 3 DS Lot 750-0406-002 (Analyzed 19Aug10) | 46.9% | 49.2% | ND | 1.0% | 1.5% |

These values are slightly lower than the DAS181 reference standard, which has 75.5±0.4% peak A. The increase in DAS181 deamidation was attributed to the high pH environment needed for specific further purification methods. The percent area of peak C increased two-fold when pH was held at 7.7 from an initial pH 5.0 for 6-7 hours. The drug substance used for phase 1 clinical trials was ~49%, since a number of phase 1 process steps were performed at pH 8.0 (Table 5, FIG. 8F).

The area of peak 1, which represents misfolded DAS181, was less in Runs A and B than in the reference standard. The percent area of peak 4 and peak F for Runs A and B drug substance were consistent with the reference standard.

Analysis of the further purification of the final drug substance produced in Runs A and B measured 15 ng/mg and 33 ng/mg, respectively (Table 6). These values are below or near the limit of quantitation (16 ng/mg) for this assay. The further purified product levels of the final drug substance were determined to be nearly identical to the levels found in products of alternative purification.

TABLE 6

ELISA Analysis Comparison of further purified products

| | HCP (ng HCP per mg DAS181) | |
|---|---|---|
| Sample | Run #3 20110523F2 | Run #4 20110613F2 |
| SP Eluate | 22,688 | 19,638 |
| HIC FT | 161 | 161 |
| UF/DF #1 Pool | 162 | 150 |
| Capto Adhere Load | 159 | 121 |
| Capto Adhere FT pH 7.7 | 41 | 37 |
| Titrated Capto Adhere FT pH 5.0 | 176 | 1,723 |
| Drug Substance | 15 | 33 |

Analysis of sialidase specific activity showed the final drug substance produced in Runs A and B was 827 U/mg and 847 U/mg, respectively (Table 7). Sialidase specific activity was comparable to the DAS181 reference standard (826 U/mg) that was run alongside the samples for quality control.

TABLE 7

Sialidase Activity Analysis Comparison

| | Specific Activity (U per mg DAS181) | |
|---|---|---|
| Sample | Run #3 20110523F2 | Run #4 20110613F2 |
| SP Eluate | 617 | 694 |
| HIC FT | 608 | 718 |
| UF/DF #1 Pool | 677 | 669 |
| Capto Adhere Load | 724 | 757 |
| Capto Adhere FT pH 7.7 | 737 | 656 |
| Titrated Capto Adhere FT pH 5.0 | 574 | 609 |
| Drug Substance | 827 | 847 |

Endotoxin analysis of the final drug substance produced in bench-scale integrated Runs A and B measured 0.018 EU/mg and 0.043 EU/mg, respectively (Table 8). Endotoxin specification for DAS181 drug substance is 0.5 EU/mg. The endotoxin levels of the drug substances produced from both runs were well below this maximum. Runs A and B were only 3.5% and 8.7% of specification limit, respectively.

TABLE 8

LAL Chromogenic Endotoxin Analysis Comparison

| | Endotoxin (EU per mg DAS181) | |
|---|---|---|
| Sample | Run #3 20110523F2 | Run #4 20110613F2 |
| SP Eluate | 1.368 | 0.240 |
| HIC FT | 0.093 | 0.126 |
| UF/DF #1 Pool | 0.003 | 0.003 |
| Capto Adhere Load* | 0.004 | 0.006 |
| Capto Adhere FT pH 7.7 | 0.006 | 0.006 |
| Titrated Capto Adhere FT pH 5.0 | 0.048 | 0.010 |
| Drug Substance | 0.018 | 0.043 |

*Run #3 shows endotoxin measurements of Capto Adhere Load Adjustment Buffer.

DAS181 purification recovery yields attained in bench-scale integrated Runs A and B were 45.9% and 55.0%, respectively (Table 89. Overall yield was greatly affected by the performance of DAS181 release via cell permeabilization and clarification recovery, and a minimal amount of DAS181 material was lost during the chromatography operations. The projected step yield was not met for primary recovery, but was higher than projected for the purification operations. In total, DAS181 recovery decreased 3.9±1.5% post-primary recovery.

TABLE 9

Integrated Runs A and B DAS181 Recovery Yields with Projected Step Yields

|  |  | Run #3 20110523F2 | | Run #4 20110613F2 | |
| --- | --- | --- | --- | --- | --- |
| Sample | Projected Step Yield | Step Yield | Overall Yield | Step Yield | Overall Yield |
| Harvest |  | 100% | 100.0% | 100% | 100.0% |
| Detergent Permeabilysate |  | 39.6% | 39.6% | 4.52% | 45.2% |
| PEI Permeabilysate | 70.0% | 171.5% | 67.9% | 194.1% | 87.8% |
| Clarified Permeabilysate |  | 72.8% | 49.5% | 71.8% | 63.0% |
| D0HC-Filtered Permeabilysate |  | 97.7% | 48.3% | 95.9% | 60.4% |
| SP Load (125% Dilution, 2M Urea) |  | — | 48.3% | — | 60.4% |
| FT | 95.0% | 0.6% | 0.3% | 0.0% | 0.0% |
| UTSP Wash |  | 2.1% | 1.0% | 0.3% | 0.2% |
| SP Eluate |  | 112.3% | 54.2% | 112.3% | 67.9% |
| HIC Load | 95.0% | — | 54.2% | — | 67.9% |
| HIC FT |  | 105.9% | 57.5% | 105.9% | 71.8% |
| UF/DF #1 Pool pH 5.0 | 95.0% | 87.8% | 50.4% | 88.5% | 63.5% |
| Titrated UF/DF #1 Pool pH 7.7 | 99.0% | 99.5% | 50.2% | 101.3% | 64.3% |
| Capto Adhere Load pH 7.7 | 90.0% | — | 50.2% | — | 64.3% |
| Capto Adhere FT pH 7.7 |  | 94.5% | 47.4% | 91.6% | 58.9% |
| Titrated Capto Adhere FT pH 5.0 | 99.0% | 97.7% | 46.3% | 97.6% | 57.4% |
| Drug Substance (UF/DF #2 Pool) | 90.0% | 99.3% | 45.9% | 95.7% | 55.0% |

Recovery of further purified products of Runs A and B was 93.1±1.5%. This was an improvement over the products of alternatively further purified products used in run #1 and #2, which yielded 89.9±2.4% recovery. Yields for the UF/DF #1 operation were lower than expected for all bench-scale integrated runs, ~88-90%. Projected step yields were exceeded for all chromatography operations.

It was concluded that the proposed phase 3 DAS181 purification process optimized with improved parameters produced drug substance that was comparable to or in some instances better than the DAS181 reference, in terms of purity, purification recovery yield, and activity. The low RP-HPLC purity issue are previously experienced was corrected with Capto Adhere chromatography in place of RP chromatography.

Example 3

Optimizing Parameters for the Reagents of Detergent Solubilization Protein Purification Various parameters of the different reagents of the detergent solubilization protocol were assayed and compared for optimization of the assay based on protein yield. First, various concentrations of Triton in combination with a limited range of SDS concentrations were selected to be evaluated for DAS181 recovery yield. Further, various combinations of sodium phosphate and EDTA pre-treatment at pH 6 for effect on DAS181 recovery by detergent permeabilization using 7% Triton X-100 and 0.1% SDS. In addition, it was determine whether duration of PEI treatment impacts the characteristics of DAS181 during hold times extending up to 5 days at room temperature. Lastly, the stability of DAS 181 clarified detergent permeabilysate, stored at 4° C. was evaluated and utilized to determine permissible hold time prior to SP chromatography for large scale manufacturing.

Methods

Detergent concentration analysis: Fermentations were aliquoted and subject to detergent solubilization purification. The detergents were added at various concentrations and agitated for 6 hours at 30° C. Supernatants were subjected to cation exchange HPLC. The relative peak areas (% of total peak area) were determined for peaks A, C, and F. DAS181 concentration was determined by comparison of the CEX total peak area to a standard of known concentration, and this concentration was normalized to the fermentation harvest yield as determined by sialidase assay to give recovery (% of harvest). Select detergent solubilized samples were clarified by addition of 10% PEI (in 50 mM potassium phosphate, 200 mM NaCl, final pH 6.0) to reach a final PEI concentration of 0.48%. Supernatants were subject to turbidity measurements and further purification.

Sodium Phosphate and EDTA Pre-Treatment Analysis

The fermentation was harvested after 24 hours induction. Dibasic sodium phosphate heptahydrate and EDTA free acid at pH 8.7 were added at various concentration combination. The samples were subject to the detergent solubilization protocol. Supernatants were subject to cation exchange HPLC. The relative peak areas (% of total peak area) were determined for peaks A, C, and F. DAS181 concentration was determined by comparison of the total peak area to a standard of known concentration, and this concentration was normalized to the fermentation harvest yield to give recovery (% of harvest).

Evaluation of PEI Clarified Permeabilisate Concentration

The fermentation was harvested after 24 hrs induction. The samples were subject to the detergent solubilization protocol. PEI was added to a final concentration of 0.5%. Samples were removed from the fermenter at various time intervals. Supernatants were subject to OD measurement and further methods of purification.

Evaluation of PEI clarified permeabilisate storage time: Starting material used in this study was further purified permeabilysate from a fermentation run. These samples were subject to further methods of purification.

Results

Detergent concentration analysis: Detergents Triton and SDS were added in various concentration combinations during the detergent solubilization protocol. The yields of DAS181 that results are summarized in Table 8.

TABLE 8

DAS 181 Release Following Treatment with Various Concentration Combinations of Triton and SDS

| | % SDS | | | | | | | | | | |
|---|---|---|---|---|---|---|---|---|---|---|---|
| % Triton | 0 | 0.1 | 0.2 | 0.25 | 0.3 | 0.35 | 0.4 | 0.45 | 0.5 | Average | StDev |
| 1 | 69.8% | 59.2% | 56.4% | 51.1% | 59.7% | 52.7% | 50.1% | 50.8% | 55.1% | 56.1% | 6.3% |
| 2 | 67.7% | 62.0% | 60.6% | 65.4% | 61.3% | 59.9% | 60.1% | 65.0% | 64.8% | 63.0% | 2.8% |
| 3 | 71.5% | 66.8% | 61.98 | 63.8% | 62.1% | 62.6% | 65.7% | 62.8% | 62.9% | 64.5% | 3.1% |
| 4 | 64.4% | 68.7% | 61.4% | 65.7% | 70.7% | 56.8% | 56.3% | 57.4% | 61.1% | 62.5% | 5.2% |
| 4.5 | 77.2% | 67.2% | 60.1% | 61.4% | 65.8% | 59.2% | 72.6% | 70.8% | 73.1% | 67.5% | 6.4% |
| 5 | 72.3% | 64.6% | 65.9% | 67.1% | 71.4% | 67.8% | 69.5% | 68.9% | 67.6% | 68.3% | 2.4% |
| 5.5 | 61.% | 71.9% | 74.2% | 70.5% | 63.9% | 66.2% | 66.7% | 64.1% | 65.3% | 67.2% | 4.2% |
| 6 | 64.% | 73.3% | 74.5% | 64.7% | 64.7% | 65.6% | 74.1% | 61.2% | 62.7% | 67.3% | 5.2% |
| 7 | 63.1% | 79.8% | 72.3% | 74.9% | 67.6% | 71.44 | 71.1% | 69.5% | 66.7% | 70.7% | 4.9% |
| 8 | 74.3% | 74.6% | 75.1% | 75.9% | 72.1% | 72.7% | 71.0% | 72.4% | 72.3% | 73.4% | 1.6% |

| | % SDS | | | | | | | | | |
|---|---|---|---|---|---|---|---|---|---|---|
| % Triton | 0 | 0.05 | 0.1 | 0.15 | 0.2 | 0.25 | 0.3 | 0.5 | Average | StDev |
| 5 | 80.5% | 76.0% | 74.0% | 75.6% | 91.5% | 76.5% | 54.4% | 70.3% | 74.8% | 10.4% |
| 6 | 77.9% | 78.1% | 77.4% | 75.7% | 73.7% | 77.6% | 71.4% | 69.5% | 75.2% | 3.3% |
| 7 | 76.6% | 76.8% | 76.4% | 73.2% | 72.9% | 71.4% | 74.5% | 70.6% | 74.0% | 2.4% |
| 8 | 75.7% | 73.2% | 77.1% | 73.8% | 72.1% | 73.8% | 71.2% | 73.3% | 73.8% | 1.9% |
| 9 | 77.3% | 79.6% | 72.2% | 74.0% | 75.1% | 74.7% | 76.3% | 75.6% | 75.6% | 2.2% |
| 10 | 78.1% | 75.9% | 77.3% | 75.5% | 69.4% | 68.2% | 71.7% | 71.7% | 73.5% | 3.7% |
| 11 | 69.0% | 70.2% | 66.7% | 69.7% | 72.4% | 70.7% | 71.8% | 67.4% | 69.7% | 2.0% |
| 12 | 73.8% | 68.3% | 71.7% | 73.4% | 69.1% | 67.5% | 67.8% | 69.5% | 70.1% | 2.5% |
| 13 | 71.9% | 71.8% | 69.2% | 65.0% | 70.4% | 69.3% | 66.2% | 65.5% | 68.7% | 2.8% |
| 14 | 68.7% | 62.2% | 58.3% | 65.0% | 62.6% | 68.7% | 67.8% | 61.3% | 64.3% | 3.8% |
| 15 | 69.8% | 66.6% | 68.1% | 66.1% | 67.7% | 66.1% | 63.9% | 60.4% | 66.1% | 2.9% |

As Triton X-100 concentration was increased from 1% to 8%, there was no clear trend in DAS181 yield as SDS concentration changes, suggesting that SDS, although itself a critical factor, did not affect yield as a factor of its concentration. At 8% Triton X-100, there was a clear increase in recovery with a tighter standard deviation with an average yield recovery of 73% across all SDS concentrations. Higher concentrations were hence investigated. A stable yield was noted from 5-9% Triton X-100. The yield began to decrease at concentrations greater than 9% Triton X-100. A trend of decreased DAS181 yield at higher SDS concentrations was also noted. It was observed during sampling that detergent treatments containing >9% Triton X-100 were more viscous than samples with lower Triton X-100 concentrations.

Treatment of samples with PEI showed a consistent yield at Triton X-100 concentrations of 5-9%, although there was variation in the assay. A slight decrease in yield was observed with 10% Triton X-100 and higher. Overall increased turbidity was observed in samples isolated from protocols which utilized increased Triton X-100 concentration. (Table 10).

TABLE 10

DAS Recovery after PEI Treatment for Various Concentrations of Detergent Combinations PEI Clarified Samples

| Sample | % Recovery | $O.D_{600\ nm}$ |
|---|---|---|
| 5.0% Triton/0.15% SDS | 66.3 | 0.216 |
| 6.0% Triton/0.15% SDS | 62.3 | 0.225 |
| 7.0% Triton/0.15% SDS | 60.7 | 0.243 |
| 8.0% Triton/0.15% SDS | 59.7 | 0.237 |
| 9.0% Triton/0.15% SDS | 64.2 | 0.332 |

TABLE 10-continued

DAS Recovery after PEI Treatment for Various Concentrations of Detergent Combinations PEI Clarified Samples

| Sample | % Recovery | $O.D_{600\ nm}$ |
|---|---|---|
| 10.0% Triton/0.15% SDS | 58.7 | 0.399 |
| 11.0% Triton/0.15% SDS | 56.9 | 0.415 |
| 12.0% Triton/0.15% SDS | 57.3 | 0.531 |
| 13.0% Triton/0.15% SDS | 57.7 | 0.533 |
| 14.0% Triton/0.15% SDS | 54.1 | 0.732 |
| 15.0% Triton/0.15% SDS | 54.5 | 0.763 |

It was concluded that optimal Triton X-100 concentrations were between 5-8%, demonstrating process tolerance to Triton concentration. DAS181 yield was consistent from 5-10% Triton X-100, while turbidity was consistent from 5-8% Triton X-100. These data support the use of Triton X-100 in the range of 5-8% in combination with 0.05-0.2% SDS.

Sodium Phosphate and EDTA Pre-Treatment Analysis

The data showed a general increase in DAS181 release as the combinations of sodium phosphate heptahydrate and EDTA increased in concentrations (Table 11). Also, little to no DAS181 release was observed in the control sample that received no pre-treatment prior to pH 6 permeabilization. Pre-treatment at pH 5 with the selected pre-treatment concentrations of 50 mM sodium phosphate and 100 mM EDTA had approximately the same percent recovery of DAS181 as the same conditions at pH 6 (Table 11).

TABLE 11

Effect of Various Detergent Permeabilizing Agents on DAS181 Recovery

| Sample | NaPi (mM) | EDTA (mM) | % Recovery (pH 6) 30 min | 60 min | 180 min |
|---|---|---|---|---|---|
| 1 | 10 | 75 | 47.6% | 49.4% | 41.7% |
| 2 | 50 | 75 | 50.6% | 49.2% | 52.5% |
| 3 | 75 | 75 | 59.4% | 58.8% | 60.2% |
| 4 | 25 | 90 | 54.4% | 56.4% | 55.4% |
| 5 | 50 | 90 | 59.5% | 55.2% | 59.6% |
| 6 | 75 | 90 | 57.5% | 56.4% | 63.2% |
| 7 | 10 | 100 | 53.8% | 52.1% | 56.8% |
| 8 | 25 | 100 | 55.7% | 56.0% | 61.5% |
| 9 | 50 | 100 | 60.0% | 58.3% | 68.3% |
| 10 | 75 | 100 | 59.3% | 59.3% | 68.1% |
| 11 | 100 | 100 | 60.8% | 62.7% | 65.4% |
| 12 | 25 | 125 | 58.9% | 54.8% | 58.8% |
| 13 | 50 | 125 | 60.6% | 60.6% | 59.6% |
| 14 | 75 | 125 | 60.1% | 61.1% | 58.8% |
| 15 | 10 | 200 | 64.9% | 64.3% | 64.9% |
| 16 | 50 | 200 | 62.9% | 67.3% | 65.4% |
| 17 | 100 | 200 | 61.9% | 87.6% | 63.2% |
| 18 | 0 | 0 | 2.3% | 2.2% | 0.0% |
| 19 (pH 5.0) | 50 | 100 | 58.5% | 63.3% | 59.6% |
| 20 (pH 8.0) | 50 | 100 | 53.2% | 61.3% | 54.5% |

It was concluded that pre-treatment combinations of sodium phosphate and EDTA are required for effective Triton X-100 and SDS permeabilization of pDAS181 E. coli to allow release of DAS181. Overall, these observations suggest that detergent permeabilization is robust over a wide range of sodium phosphate and EDTA concentrations, pH conditions, and incubation time. The combination of 50 mM sodium phosphate and 100 mM EDTA at pH6 was selected as the optimal pretreatment concentrations.

Evaluation of PEI Clarified Permeabilisate

Clarified supernatants from PEI treatment held at room temperature increase in turbidity with extended hold times (Table 12). The increase in turbidity was greatest in samples that had the shortest PEI treatment time, and turbidity changed least in samples that had longer PEI treatment times; confirming that longer PEI treatment times resulted in clarified material with reduced precipitate formation. PEI treatments>7 hrs result in the smallest turbidity increase within 24 hrs, and PEI treatments>20 hrs result in the best stability (OD600 nm<2.0) up to the longest duration measured, which was 120 hrs. PEI treatments <6 hrs resulted in turbidity OD600 nm>3.0 at 120 hours, and slightly increased turbidity at 24 hrs when compared to PEI treatments>7 hrs.

DAS181 recovery was determined immediately after PEI treatment and centrifugation. The recovery ranged from 81 to 95% (Table 4 and FIG. 2). The majority of the sample points have consistent recovery between 83 to 89%. The ratios of the DAS181 variants measured by the rapid CEX-HPLC assay (Peaks A, C and F) were constant within the error of the assay (Table 13). The main DAS181 peak (A) was between 79.93% and 81.63% for all PEI treatments. Peak C was between 10.20% and 12.06%, and peak F ranged between 7.81% and 8.91%. These data show long PEI treatment time does not adversely affect DAS181 product quality.

TABLE 12

Effect of PEI Treatment Duration and Post-Clarification Hold Time on Permeabilisate Turbidity

| Hold After PEI Treatment. (Hrs) | 0.5% PEI Treatment (Hrs) | | | | | | | | | | | | | |
|---|---|---|---|---|---|---|---|---|---|---|---|---|---|---|
| | 0 | 1 | 2 | 3 | 4 | 5 | 6 | 7 | 8 | 9 | 10 | 12 | 20 | 24 |
| 0 | 0.20 | 0.22 | 0.24 | 0.27 | 0.27 | 0.27 | 0.28 | 0.23 | 0.29 | 0.27 | 0.26 | 0.27 | 0.32 | 0.35 |
| 24 | 0.91 | 0.92 | 0.90 | 0.95 | 0.90 | 0.93 | 0.80 | 0.75 | 0.74 | 0.74 | 0.69 | 0.71 | 0.69 | ND |
| 48 | 2.99 | 2.81 | 2.23 | 2.42 | 1.62 | 2.45 | 2.12 | ND | ND | ND | ND | ND | 1.72 | 1.68 |
| 120 | 3.07 | 3.53 | 2.89 | 3.14 | 3.25 | 3.23 | 3.00 | ND | ND | ND | ND | ND | 1.90 | 1.90 |

ND = Not determined

TABLE 13

DAS181 Recovery and DAS181 Variant levels Immediately Following PEI Treatment.

| Parameter Measured | 0.5% PEI Treatment (Hrs) | | | | | | | | | | | | | |
|---|---|---|---|---|---|---|---|---|---|---|---|---|---|---|
| | 0 | 1 | 2 | 3 | 4 | 5 | 6 | 7 | 8 | 9 | 10 | 12 | 20 | 24 |
| DAS181 % recovery | 81% | 86% | 88% | 95% | 83% | 84% | 86% | 87% | 88% | 89% | 87% | 87% | 87% | 88% |
| Peak A | 81.43% | 80.49% | 81.02% | 80.60% | 80.00% | 81.08% | 80.31% | 80.38% | 81.47% | 81.49% | 81.49% | 80.89% | 79.93% | 81.63% |
| Peak C | 10.20% | 10.77% | 10.33% | 10.73% | 11.21% | 10.27% | 10.79% | 10.86% | 10.37% | 10.49% | 10.41% | 10.67% | 12.06% | 10.55% |
| Peak F | 8.37% | 8.74% | 8.65% | 8.67% | 8.79% | 8.65% | 8.91% | 8.76% | 8.16% | 8.02% | 8.10% | 8.44% | 8.01% | 7.81% |

It was concluded that following 24 hours of hold time at room temperature, clarified permeabilisate turbidity remained low for all treatment times, but was lowest for times ≥6 hrs. After 48 hrs hold, the increase in turbidity is least for the longer PEI treatments. The ratios of DAS181 variants did not change with PEI treatment duration. These data indicate that a PEI treatment time of over 6 hours allowed good stability of the protein for at least 24 hours. This study also suggests that PEI clarified supernatants can be held at least 24 hours without affecting filterability.

Evaluation of PEI Clarified Permeabilisate Storage Time

Turbidity of the additionally purified clarified detergent permeabilysate did not increase after 1 week of storage at 4° C. (Table 14). The turbidity increased by 46% from week 1 to week 2 of storage and about 7% from week 2 to week 3.

TABLE 14

Turbidity of Clarified Detergent Permeabilysate

| Clarified Detergent Permeabilysate | Turbidity (OD$_{600}$) |
|---|---|
| T = 0 | 0.66 |
| 1 week @ 4° C. | 0.68 |
| 2 weeks @ 4° C. | 1.25 |
| 3 weeks @ 4° C. | 1.34 |

SP FF chromatography recovery was as expected for each run with some variability in loss of DAS 181 to FT and UTSP wash (Table 15). Approximately 5-6% loss was observed upon further purification, while almost no DAS 181 was observed following further purification.

15: Yield and mass balance for Analysis Comparison of Products from Further Purification

| Clarified Detergent Permeabilysate | Flow-Through (FT) | UTSP wash | SP Eluate | Mass Balance |
|---|---|---|---|---|
| T = 0 | 0.6% | 2.1% | 112.3% | 114.8% |
| 1 week @ 4° C. | 5.5% | 3.8% | 97.2% | 106.5% |
| 2 weeks @ 4° C. | 6.0% | 3.5% | 96.3% | 105.8% |
| 3 weeks @ 4° C. | 4.7% | 0.2% | 104.4% | 109.3% |

Purity analysis by additional, alternative purification methods showed that the SP eluates prepared after 1-3 week hold at 4° C. were similar to the SP eluate prepared with fresh feed stock (Table 16). Relatively high purity through the further purification was observed.

TABLE 16

Clarified Detergent Permeabilysate Stability Post Further Purification Summary

| Clarified Detergent Permeabilysate | SP Eluate | | |
|---|---|---|---|
| | RP-HPLC Purity | SEC-HPLC (% Monomer) | HCP (ng/mg) |
| T = 0 | 94.5% | 99.8% | 22,688 |
| 1 week @ 4° C. | 95.5% | 99.7% | 9,692 |
| 2 weeks @ 4° C. | 94.4% | 99.7% | 8,950 |
| 3 weeks @ 4° C. | 94.4% | 99.8% | 12,120 |

Figure 9:
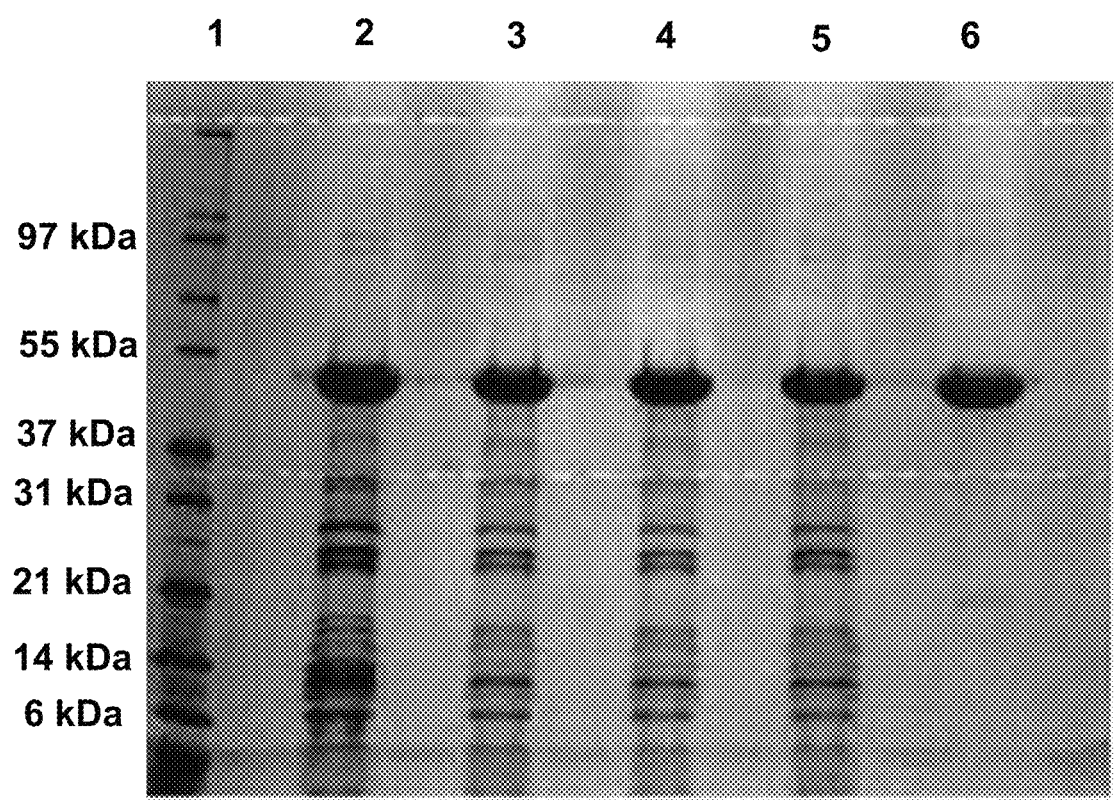
FIG. 9 is an SDS-PAGE analyses of DAS 181 stability over several weeks of storage (lane 1=size markers; lane 2=Time O; lane 3=1 week storage; 4=2 weeks storage; lane 5=3 weeks storage; lane 6=control).

Results following further purification revealed a slight increase in deamidation of DAS181 as seen by increasing % Peak C in the SP eluates produced after 2 weeks of storage (Table 16). This degree of deamidation is consistent with recent Bench Integrated run samples of further purification which can all be considered effectively T=0 samples for clarified detergent permeabilysate storage. SDS-PAGE analysis showed consistent stability between products of alternate further purification (FIG. 9). Impurity band intensity appeared close to identical in further purified samples after 1, 2 and 3 weeks of 4° C. storage. The T=0 sample impurities appeared to be more intense than the other samples, which may be due to slightly more heavily loaded sample.

It was determined that there was no decrease in the purity of further purified samples produced from feed stock held up to 3 weeks at 4° C. CEXHPLC analysis however did show a slight increase in deamidation (peak C) after 2 weeks of storage. Clarified detergent permeabilysate is stable at 4° C. for up to one week as shown by the purity of the further purified samples obtained.

DAS181 Sequences
DAS 181 (without amino terminal Met)
(SEQ ID NO: 1)
GDHPQATPAPAPDASTELPASMSQAQHLAANTATDNYRIPAITTAPNGDL

LISYDERPKDNGNGGSDAPNPNHIVQRRSTDGGKTWSAPTYIHQGTETGK

KVGYSDPSYVVDHQTGTIFNFHVKSYDQGWGGSRGGTDPENRGIIQAEVS

TSTDNGWTWTHRTITADITKDKPWTARFAASGQGIQIQHGPHAGRLVQQY

TIRTAGGAVQAVSVYSDDHGKTWQAGTPIGTGMDENKVVELSDGSLMLNS

RASDGSGFRKVAHSTDGGQTWSEPVSDKNLPDSVDNAQIIRAFPNAAPDD

PRAKVLLLSHSPNPRPWSRDRGTISMSCDDGASWTTSKVFHEPFVGYTTI

AVQSDGSIGLLSEDAHNGADYGGIWYRNFTMNWLGEQCGQKPAKRKKKGG

KNGKNRRNRKKKNP

DAS 181 (with amino terminal Met)
(SEQ ID NO: 2)
MGDHPQATPAPAPDASTELPASMSQAQHLAANTATDNYRIPAITTAPNGD

LLISYDERPKDNGNGGSDAPNPNHIVQRRSTDGGKTWSAPTYIHQGTETG

KKVGYSDPSYVVDHQTGTIFNFHVKSYDQGWGGSRGGTDPENRGIIQAEV

STSTDNGWTWTHRTITADITKDKPWTARFAASGQGIQIQHGPHAGRLVQQ

YTIRTAGGAVQAVSVYSDDHGKTWQAGTPIGTGMDENKVVELSDGSLMLN

SRASDGSGFRKVAHSTDGGQTWSEPVSDKNLPDSVDNAQIIRAFPNAAPD

DPRAKVLLLSHSPNPRPWSRDRGTISMSCDDGASWTTSKVFHEPFVGYTT

IAVQSDGSIGLLSEDAHNGADYGGIWYRNFTMNWLGEQCGQKPAKRKKKG

GKNGKNRRNRKKKNP

Other Embodiments

It is understood that while the invention has been described in conjunction with the detailed description thereof, the foregoing description is intended to illustrate and not limit the scope of the invention, which is defined by the scope of the appended claims. Other aspect, advantages, and modifications are within the scope of the following claims.

The invention claimed is:

1. A composition comprising a polypeptide comprising the amino acid sequence of SEQ ID NO: 1 or 2 made by a method comprising:
   (a) providing a liquid culture of a cell expressing the polypeptide;
   (b1) contacting the culture with an inorganic salt; holding the culture containing the added inorganic salt for at least 10 minutes; contacting the culture containing the added inorganic salt with a chelating agent; or
   (b2) contacting the culture with an inorganic salt and a chelating agent;
   (c) holding the culture containing the added inorganic salt and added chelating agent for at least 10 minutes;
   (d) contacting the culture containing the added inorganic salt and the added chelating agent with a detergent;
   (e) contacting the culture containing the added inorganic salt, the added chelating agent and the added detergent with a precipitating agent;
   (f) holding the culture containing the added inorganic salt, the added chelating agent and the added detergent for at least 1 hour; and
   (g) subjecting the culture comprising the added inorganic salt, the added chelating agent, the added detergent and the added precipitating agent to a method to remove a substantial portion of the cellular debris, thereby providing a supernatant composition comprising the polypeptide;
   wherein the method does not comprise: (i) mechanical disruption of the cells, (ii) removing substantially all of the culture media, or (iii) addition of an enzyme that degrades cell wall material.

2. The composition of claim 1, wherein the inorganic salt is selected from: sodium phosphate, ammonium sulfate, and sodium chloride.

3. The composition of claim 1, wherein the detergent comprises a detergent selected from the group consisting of: Triton, SDS, CHAPS 3, Nonidet P40, n-Octylglucoside, and Tween-20.

4. The composition of claim 1, wherein the detergent is a mixture of two detergents selected from the group consisting of: Triton, SDS, CHAPS 3, Nonidet P40, n-Octylglucoside, and Tween-20.

5. The composition of claim 1, wherein the precipitating agent is selected from a group consisting of: polyethyleneimine, ammonium salt, polyethylene glycol, TCA and ethanol.

6. The composition of claim 1, wherein the inorganic salt is sodium phosphate at 10 to 100 mM.

7. The composition of claim 1, wherein the chelating agent is EDTA at 75 to 200 mM.

8. The composition of claim 1, wherein the detergent is Triton X-100 at 5-8% and SDS at 0.05-0.2% percent.

9. The composition of claim 1, wherein the precipitating agent is polyethyleneimine at 0.5 percent.

10. The composition of claim 1, wherein the inorganic salt of step (b1) or (b2) is at least at a concentration of 10 mM.

11. The composition of claim 1, wherein the inorganic salt of step (b1) or (b2) is at least at a concentration of 20 mM.

12. The composition of claim 1, wherein the inorganic salt of step (b1) or (b2) is at least at a concentration of 30 mM.

13. The composition of claim 1, wherein the inorganic salt of step (b1) or (b2) is at least at a concentration of 40 mM.

14. The composition of claim 1, wherein the inorganic salt of step (b1) or (b2) is at least at a concentration of 50 mM.

15. The composition of claim 1, wherein the inorganic salt of step (b1) or (b2) is at least at a concentration of 60 mM.

16. The composition of claim 1, wherein the inorganic salt is sodium phosphate at 10 to 100 mM, the chelating agent is EDTA at 75 to 200 mM, the detergent is Triton X-100 at 5-8% and SDS at 0.05-0.2% percent, and the precipitating agent is polyethyleneimine at 0.5 percent.

17. The composition of claim 1, wherein the gram negative bacterial cell is *E. coli*.

18. The composition of claim 1, wherein the method of step (g) is subjecting the supernatant composition comprising the polypeptide to chromatography.

* * * * *